United States Patent
Cronin et al.

(10) Patent No.: US 10,478,589 B2
(45) Date of Patent: Nov. 19, 2019

(54) WEARABLE DEVICE FOR SLEEP ASSISTANCE

(71) Applicant: KONINKLIJKE PHILIPS N.V., Eindhoven (NL)

(72) Inventors: John Cronin, Bonita Springs, FL (US); Christopher Huffines, Williston, VT (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 234 days.

(21) Appl. No.: 15/559,448

(22) PCT Filed: Mar. 21, 2016

(86) PCT No.: PCT/EP2016/056177
§ 371 (c)(1),
(2) Date: Sep. 19, 2017

(87) PCT Pub. No.: WO2016/150924
PCT Pub. Date: Sep. 29, 2016

(65) Prior Publication Data
US 2018/0110959 A1    Apr. 26, 2018

Related U.S. Application Data

(60) Provisional application No. 62/137,965, filed on Mar. 25, 2015.

(51) Int. Cl.
*A61M 21/00*    (2006.01)
*A61M 21/02*    (2006.01)
(Continued)

(52) U.S. Cl.
CPC ........... *A61M 21/02* (2013.01); *A61B 5/4806* (2013.01); *A61B 5/6801* (2013.01); *G06F 1/163* (2013.01);
(Continued)

(58) Field of Classification Search
CPC ....... A61B 5/4812; A61B 5/68; A61B 5/4806; A61B 5/4809; A61M 21/00
See application file for complete search history.

(56) References Cited

U.S. PATENT DOCUMENTS

| | | |
|---|---|---|
| 2010/0099954 A1 | 4/2010 | Dickinson |
| 2013/0303837 A1 | 11/2013 | Berka |
| 2014/0316191 A1 | 10/2014 | De Zambotti |

FOREIGN PATENT DOCUMENTS

| | | |
|---|---|---|
| EP | 2460464 A1 | 6/2012 |
| WO | WO2013061415 A1 | 5/2013 |

(Continued)

OTHER PUBLICATIONS

Kingsley J. et al., "Eat, Sleep, Wear, Repeat—Virgin Media launches 'KipstR' the tech that controls TV as you sleep", Dec. 18, 2014 (Dec. 18, 2014), XP055278326.
(Continued)

*Primary Examiner* — Omkar A Deodhar

(57) ABSTRACT

A wearable device (105) for sleep assistance includes at least one sensor (115) to detect one or several vital signs of a user of the wearable device, a memory (155) to store a set of sleep aid techniques, and an interface to receive a selection of a sleep aid technique from the set of sleep aid techniques. Each aid sleep technique includes instructions facilitating the user to fall asleep and is associated with a doze-off time estimated for the sleep aid technique to affect the user following the instructions. The wearable device also includes a processor to update the doze-off time based on the vital signs of the user, to determine, based on the updated doze-off time, a schedule for executing at least one predetermined action, and to execute the predetermined action according to the schedule.

15 Claims, 18 Drawing Sheets

(51) Int. Cl.
*A61B 5/00* (2006.01)
*G06F 1/16* (2006.01)
*G09B 5/02* (2006.01)
*G09B 5/04* (2006.01)
*G09B 5/06* (2006.01)
*G09B 19/00* (2006.01)
*A61B 5/1455* (2006.01)

(52) U.S. Cl.
CPC .............. *G09B 5/02* (2013.01); *G09B 5/04* (2013.01); *G09B 5/06* (2013.01); *G09B 19/00* (2013.01); *A61B 5/14552* (2013.01); *A61B 5/4809* (2013.01); *A61B 5/4812* (2013.01); *A61M 2021/0027* (2013.01); *A61M 2021/0044* (2013.01); *A61M 2205/3546* (2013.01); *A61M 2205/3584* (2013.01); *A61M 2205/50* (2013.01); *A61M 2205/505* (2013.01); *A61M 2205/52* (2013.01); *A61M 2230/50* (2013.01); *A61M 2230/63* (2013.01)

(56) References Cited

FOREIGN PATENT DOCUMENTS

| | | |
|---|---|---|
| WO | WO2013170032 A2 | 11/2013 |
| WO | WO2015006364 A2 | 1/2015 |

OTHER PUBLICATIONS

Observations on the PCT International Search Report and the Written Opinion of International Application No. PCT/EP2016/056177, Pavan Kapoor, dated Dec. 6, 2016.
PCT International Search Report, International Application No. PCT/EP2016/056177, dated Mar. 21, 2016.

Sensor/technique concept 200

220

| | | Sensor* | Microphone 220A | Camera 220B | Accelerometer 220C | Skin conductance 220D | Peripheral device 220E | Touchscreen 220F | Questionnaire | ... |
|---|---|---|---|---|---|---|---|---|---|---|
| Sleep technique | | | | | | | | | | |
| Inhale through left nostril | 210A | | x | x | x | | | | x | |
| Squeeze and relax muscles | 210B | | | x | x | x | | | x | |
| Try to stay awake | 210C | | | | | | | x | x | |
| Rewind your day | 210D | | x | | | | | | x | |
| Roll your eyes | 210E | | | x | x | | | | x | |
| Just imagine | 210F | | | | | | | | x | |
| Hum to yourself | 210G | | x | | x | | | | x | |
| Press here | 210H | | | x | x | | x | x | x | |
| Find your trigger | 210I | | | | | | | | x | |
| Take a breather | 210J | | x | x | x | | x | | x | |
| Make a worry list | 210K | | x | x | x | x | x | | x | |
| . . . | | | | | | | | | | |

*Sensors includes both actual and virtual sensors

FIG. 2B

| Time after sleep | 310 | Environment trigger | 320 |
|---|---|---|---|
| 0 | 330 | Lock doors | |
| 1 | 340 | Dim all lights to 0 | |
| 1 | 350 | Lower all audio device volumes to 0 | |
| . . . | | | |

Wearable environment database 300

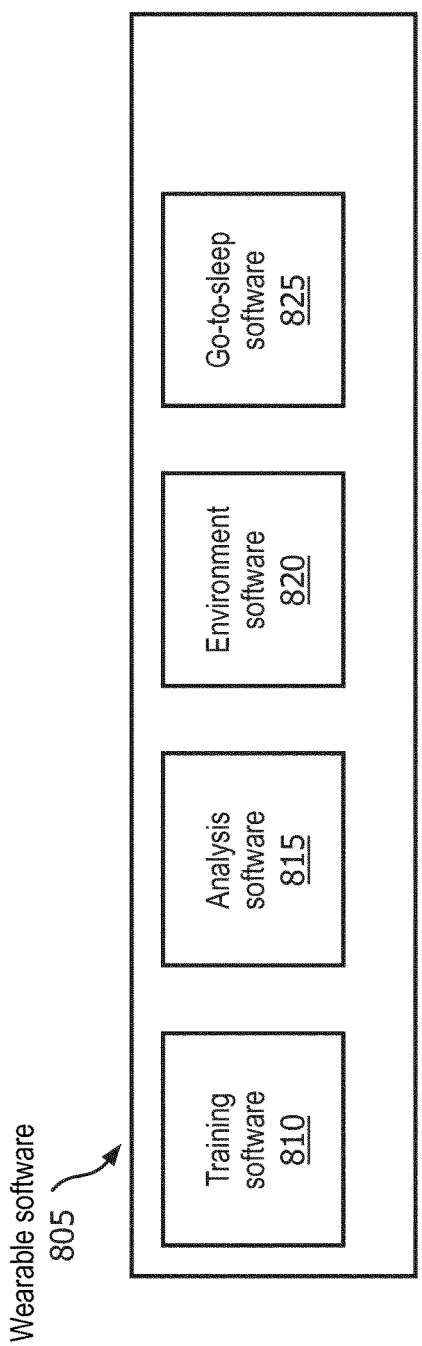

Wearable sensor data database 1100

| Date 1110 | Time 1120 | % Doze 1130 | Technique data type 1 1140 | Technique data point 1 1150 | ... | Technique data type n 1160 | Technique data point n 1170 |
|---|---|---|---|---|---|---|---|
| 02-10-2015 | 2059 | 5 | RWYDPulse | 64 | | RWYDBP | 120/80 |
| 02-10-2015 | 2100 | 6 | RWYDPulse | 63 | | RWYDBP | 120/80 |
| 02-10-2015 | 2101 | 7 | RWYDPulse | 64 | | RWYDBP | 118/78 |
| 02-10-2015 | 2102 | 15 | RWYDPulse | 60 | | RWYDBP | 115/77 |
| 02-10-2015 | 2103 | 25 | RWYDPulse | 58 | | RWYDBP | 114/75 |
| 02-10-2015 | 2104 | 35 | RWYDPulse | 56 | | RWYDBP | 110/71 |
| 02-10-2015 | 2105 | 50 | RWYDPulse | 54 | | RWYDBP | 106/68 |
| 02-10-2015 | 2106 | 75 | RWYDPulse | 53 | | RWYDBP | 102/66 |
| 02-10-2015 | 2107 | 100 | RWYDPulse | 52 | | RWYDBP | 100/65 |
| ... | | | | | | | |

Wearable Tipping Point database 1200

| Date 1210 | Time 1220 | Time before sleep (minutes) 1230 | Time after start (minutes) 1235 | % Doze 1240 | Technique data type 1 1245 | Technique data point 1 1250 | . . . | Technique data type n 1255 | Technique data point n 1260 |
|---|---|---|---|---|---|---|---|---|---|
| 02-07-2015 | 2100 | 5 | 3 | 14 | RWYDPulse | 61 | | RWYDBP | 115/78 |
| 02-08-2015 | 2106 | 6 | 4 | 15 | RWYDPulse | 60 | | RWYDBP | 115/77 |
| 02-09-2015 | 2100 | 5 | 2 | 15 | RWYDPulse | 59 | | RWYDBP | 114/76 |
| 02-10-2015 | 2102 | 5 | 3 | 15 | RWYDPulse | 60 | | RWYDBP | 115/77 |

| Wearable user sleep profile 1300 | Sleep aid technique 1310 | Predicted time before sleep (minutes) 1320 | Predicted time after start (minutes) 1330 | Technique data type 1 1340 | Technique average data point 1 1350 | ... | Technique data type n 1360 |
|---|---|---|---|---|---|---|---|
| | Inhale through left nostril | 8 | 5 | ITLNResp | 40 | ... | ITLNBP |
| | Squeeze and relax muscles | 10 | 13 | SRMPulse | 65 | ... | SRMResp |
| | Try to stay awake | 6 | 6 | TTSAVibrate | 8 | ... | None |
| | Rewind your day | 5 | 3 | RWYDPulse | 60 | ... | RWYDBP |
| | Roll your eyes | 7 | 15 | RYERolls | 15 | ... | None |
| | Just imagine | 10 | 25 | JIQuest | 3 | ... | None |
| | Hum to yourself | : | : | HTYMic | : | ... | HTYPulse |
| | Press here | : | : | PHMuscleTension | : | ... | PHPulse |
| | Find your trigger | 15 | 4 | FYTQuest | 10 | ... | None |
| | Take a breather | : | : | TABResp | : | ... | None |
| | Make a worry list | 7 | 10 | MAWLPulse | 61 | ... | MAWLBP |

| Technique average data point n 1370 | Instructions to user 1380 |
|---|---|
| 116/79 | Lie on your left side. Place a finger over your right nostril. Begin slow, deep breathing. |
| 45 | Lie on your back. Take slow, deep breaths. Starting with your toes and working toward your head, squeeze and release each muscle groups. |
| . . | Keep your eyes wide open. Mentally challenge yourself to stay awake (don't worry, your brain will try to do the opposite). |
| 115/77 | Think back over your day. Starting with now, try to remember every mundane detail of the day. |
| . . | Close your eyes. Roll your eyes three times. Repeat as necessary |
| . . | Imaging yourself in a 'happy place' such as a tropical paradise or a strawberry field. |
| . . | Close your eyes, relax your shoulders, relax your jaw but keep your mouth closed. Hum out on each breath. |
| . . | <Display PressurePoint.jpeg>. Press the pressure points indicated in the picture. Hold for 20 seconds, then press another. |
| . . | Please perform your trigger action. |
| . . | Synch your breath synchronizer device. Breathe in an out with the device. |
| 115/77 | Think through all the things that your need to do or are worrying about. Write down your list, if you want. |

WEARABLE DEVICE FOR SLEEP ASSISTANCE

CROSS-REFERENCE TO RELATED APPLICATIONS

The present application claims the priority benefit under 35 U.S.C. § 371 of international patent application no. PCT/EP2016/056177, filed Mar. 21, 2016, which claims the priority benefit of U.S. provisional application 62/137,965 filed Mar. 25, 2015 and entitled "Doze Off Wearable," These applications are hereby incorporated by reference herein in their entirety.

TECHNICAL FIELD

This disclosure concerns wearable technology. More particularly, but not exclusively, the present disclosure concerns smart wearable devices assisting users to fall asleep.

BACKGROUND

Wearable technology, wearable devices, or simply "wearables" refer to a new class of electronic systems that can provide ubiquitous data acquisition through a variety of unobtrusive sensors. While the sensors provide information about changes in the environment, human activity or health status, there are significant challenges to the coordination, communication, and computation over the ubiquitously collected data. Furthermore, in order to synthesize the information to create useful knowledge or recommendations to consumer end-users many sources of information complementary and in addition to the collected sensor information are needed. These unconventional combinations of information sources require new designs in the hardware and the software components. Some wearable devices, e.g., wearables like Kipster™ device) try to detect when a user falls asleep. However, sleep detection that relies on vital signs of the user suffers from inter-subject differences making the detection difficult. For example, low activity tasks, such as reading or watching television, can result in the vital signs of the user similar to the signs associated with the sleeping user. In those situations, actions selected based on assumption that the user is asleep can lead to an undesirable result. Hence more improvement is needed in this regard.

SUMMARY

Some embodiments are based on recognition that different sleep aid techniques can play a role in shaping sleeping behavior and health of the people of the modern world. For example, different sleep aid techniques can help to reduce blood pressure and calm a user, relax muscles and prepare a body of the user to sleep. To that end, some embodiments are based on recognition that wearable device can be advantageously configured to help the users of the wearable device to fall asleep. This is because, the wearable device can include both an interface that can render the instructions of a sleep aid technique to the user and one or several sensors that can detect vital signs of the user suitable for evaluating the effectiveness of the instructions.

Some embodiments are based on realization that a correlation between the vital signs and doze-off stages of the user needs to be determined for the user performing the instructions of the sleeping aid technique. In such a manner, the correlation is determined for specific actions of the user that wants for fall asleep and is more accurate that a correlation determined for arbitrarily actions. As used herein, a doze-off stage describes a condition or stage of the user trying to fall asleep, i.e., a stage during a period between a user has started to fall asleep to finally being asleep.

For example, the invocation of the sleeping aid technique can serve as an indication of the intentions of the user to fall asleep. In addition, the period of time estimated for the sleep aid technique to affect the user following the instructions of the sleep aid technique can be predetermined and/or learn over time based on tracking the vital signs of the user following the instruction. This period of time is referred herein as a doze-off time. The doze-off time can be used to schedule the actions to be executed upon or during falling asleep. Because the doze-off time is determined for a specific sleep aid technique, the accuracy of scheduling the actions for different doze-off stages of the user is increased.

Additionally, the doze-off time can be updated while the user follows the instructions of the sleep aid technique. For example, the update can be based on differences in physiological conditions of the user on different days, which can be detected based on the vital signs of the user. For example, a correlation between at least some values of the vital signs of the user with fractions of the doze-off time can be determined. For example, such a correlation can be a regression function trained during multiple invocations of the sleeping aid technique. For example, if vital signs determined at a half of a period of the doze-off time indicate that the user is more active than is prescribed by the correlation, the doze-off time can be extended.

Additionally or alternatively, the update can be based on differences in dedication and/or persistence of the user to follow the instruction. For example, the user can select the sleep aid technique, but then decide to stay awake a little bit longer. To that end, at least one embodiment tracks the actions of the user to extend the doze-off time for a period of time when the user is not following the instructions of the sleep aid technique. This gives an additional advantage that the user of the device can still perform different actions even after the sleep aid technique is invoked and the device takes care of such action, thereby not stressing the user.

Wearable devices for sleep assistance are provided.

Various embodiments are directed to a wearable device that includes at least one sensor to detect one or several vital signs of a user of the wearable device; a memory to store a set of sleep aid techniques, each aid sleep technique includes instructions facilitating the user to fall asleep and is associated with a doze-off time estimated for the sleep aid technique to affect the user following the instructions; an interface to receive a selection of a sleep aid technique from the set of sleep aid techniques and to render the instructions of the selected sleep aid technique to the user; and a processor to update the doze-off time based on the vital signs of the user, to determine, based on the updated doze-off time, a schedule for executing at least one predetermined action, and to execute the predetermined action according to the schedule.

Various embodiments are directed to a method for sleep assistance to a user of a wearable device that includes detecting one or several vital signs of the user of the wearable device; selecting a sleep aid technique associated with one or more instructions facilitating the user to fall asleep and a doze-off time estimated for the sleep aid technique to affect the user following the instructions; updating the doze-off time based on the vital signs of the user; determining, based on the updated doze-off time, a schedule for executing at least one predetermined action; and executing the predetermined action according to the schedule, wherein at least some steps of the method are performed by a processor of the wearable device.

Various embodiments are directed to a non-transitory computer readable storage media embodied thereon a program executable by a processor for performing a method that includes executable instructions for detecting one or several vital signs of the user of the wearable device; for selecting a sleep aid technique associated with one or more instructions facilitating the user to fall asleep and a doze-off time estimated for the sleep aid technique to affect the user following the instructions; for updating the doze-off time based on the vital signs of the user; for determining, based on the updated doze-off time, a schedule for executing at least one predetermined action; and for executing the predetermined action according to the schedule.

BRIEF DESCRIPTION OF THE DRAWINGS

FIG. 2B illustrates a chart of exemplary sensor and sleep technique relationships.

FIG. 8A illustrates an exemplary wearable software module.

FIG. 8B illustrates an exemplary process performed upon execution of a wearable software module by a processor of a wearable device.

FIG. 11 illustrates an exemplary wearable sensor data database.

FIG. 12 illustrates an exemplary wearable tipping point database.

FIG. 13 illustrates an exemplary wearable user sleep profile.

DETAILED DESCRIPTION

Wearable devices that predict the context in which they are used based on previously tracked user input, and methods associated with the same, are provided. The wearable device may be any kind of wearable device, such as one primarily intended to be worn around a user's neck (e.g., a necklace), arm (e.g., an armband), head (e.g., hat, helmet, headband, or headlamp), leg, chest, or waist (e.g., a belt or body band), foot (e.g., a shoe or sock), ankle or knee (e.g., a knee brace), or any other area of a user's body. The wearable device may also be a device that is primarily intended to be held in a user's hand or stored in a user's pocket. The wearable device may also be a device meant to be worn over the skin (e.g., a patch) or under the skin (e.g., an implant).

The wearable devices (e.g., an Apple Watch™ device) may include, as implemented in various systems, methods, and non-transitory computer-readable storage media, may predict when a wearable device user will fall asleep based on previously recorded and received sleep data, and methods associated with the same, are provided. A wearable device may include a processor, a sensor that records data associated with a user of the wearable device, and memory storing executable instructions. By way of executing the instructions, the wearable device can assist the user of the wearable device to fall asleep and execute one or more predetermined actions upon or during falling asleep. Specifically, according to various embodiments, the wearable device allows the user to select and to follow the instructions of a sleep aid technique and to schedule an execution of the action based on doze-off time associated with the selected sleep aid instruction. The present technology increases the utility of wearable devices data in numerous ways, including enhancing user convenience, user education, and sleep data collection. The technology may also give a user more precise control over his or her environment when falling asleep.

Figure 1A:
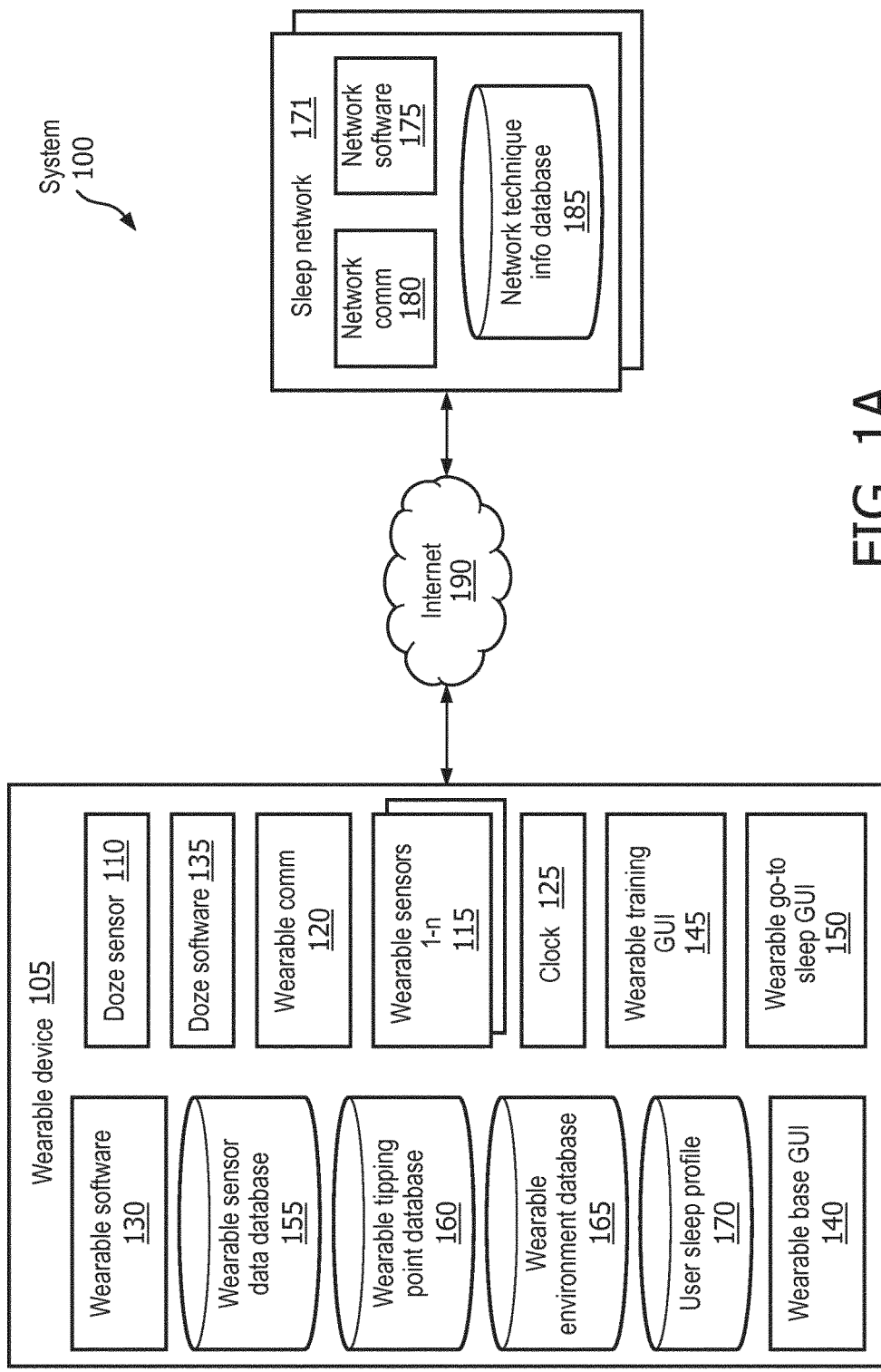
FIG. 1A illustrates an exemplary system for predicting when a wearable device user will fall asleep.

FIG. 1A illustrates an exemplary system for including a wearable device according to some embodiments assisting a user of the wearable device to fall asleep. The system 100 includes a wearable device communicatively coupled to one or more sleep networks 171. The one or more sleep networks may include one or more sleep network devices (e.g., a network server, a database server, gateways, switches, etc.) and include network software 175, a network communication interface 180, and a network technique database 185. The wearable device may be coupled to the one or more sleep networks by way the Internet or another type of network 190 (e.g., a wide area network, a local area network, or other type of network).

The wearable device may include a plurality of components. The components may be communicatively coupled to one another through one or more buses. The plurality of components may include a processor, memory, a power supply (e.g., a rechargeable lithium ion battery), a display (e.g., an LCD, LED, e-paper, or electronic ink type display), a doze sensor 110 and any number of additional sensors labeled in FIG. 1A as "wearable sensors 1-$n$" 115. Examples of the doze sensor 110 and/or the wearable sensors 115 include an activity sensor, a pulse sensor, a blood pressure sensor, a heart rate sensor, a temperature sensor, or other sensor to detect one or several vital signs of the user of the wearable device. The wearable device may also include a wired or wireless network communications module 120 (e.g., a USB port module, a FireWire port module, a Lightnight port module, a Thunderbolt port module, a Wi-Fi connection module, a 3G/4G/5G/LTE cellular connected module, a Bluetooth connection module, a lower powered Bluetooth connection module, a ZigBee module, a near field communication module, etc.). The doze sensor 110 may track a user's sleep behavior, including when the user is beginning to fall asleep and/or following the instructions of the selected sleep aid technique.

Wearable sensors 1-n 115 may include sensors that record other data about the user and/or his or her environment. A pulse sensor may include, for instance, a pulse oximeter device that records pulse, blood pressure, and blood oxygen level. A motion sensor may include an accelerometer that records a user's motion along one or more axes. A thermometer sensor may include a thermometer that records the user's temperature or the ambient temperature in the user's local environment. The components may further include a global position system ("GPS") module and/or a clock 125. The clock 125 may be a system clock that records date and time data and supplies the data to the wearable device.

The wearable device may be operable to store in memory, and the processor of the wearable device may be operable to execute, a wearable device operating system ("OS"), a wearable software module 130, and a doze software module 135. In some embodiments, the doze software module 135 may be incorporated within the wearable software module. The OS may be, for example, a Microsoft Windows™, Google Android™, or Apple™ OS. As discussed later in the context of FIG. 8A, the wearable software module may include a plurality of executable submodules. The software submodules may include a training software submodule 810, an analysis software submodule 815, an environment software submodule 820, and a go-to-sleep software submodule 825. The wearable software module may further include a plurality of graphical user interface ("GUI") sub-modules that, when executed by the processor of the wearable device, render and display one or more GUIs on a display of the wearable device. The one or more GUI software submodules may include a wearable base GUI 140 submodule, a wearable training GUI submodule 145, a go-to-sleep GUI submodule 150, or other GUI submodules.

By way of executing the GUI submodules, the wearable device may display a wearable base GUI 140, a wearable training GUI 145, and a wearable go-to-sleep GUI. The wearable device may further be operable to store one or more databases in memory (e.g., a wearable sensor data database 155, a wearable tipping point database 160, a wearable environment database 165, and a user sleep profile database 170). The wearable sensor data database 155 may store sensor data recorded by the wearable device by way of the one or more sensors 110 & 115. The wearable tipping point database 160 may store specific data points from the wearable sensor data database 155. The specific data points may concern a predictable amount of time remaining until a user of the wearable device falls asleep or "dozes off." The wearable environment database 165 may store information about activities that the user previously selected to be performed when the user begins to fall asleep. The user sleep profile database 170 may store information about a plurality of sleep aid techniques and data related to the same.

The wearable base GUI 140 may provide a plurality of selectable or fillable elements through which a user may select subsequent GUIs (e.g., the wearable training GUI, the wearable go-to-sleep GUI, or other GUIs). The wearable training GUI 145 may provide a plurality of selectable or fillable elements through which a user may select and activate one or more sleep techniques. By way of the wearable training GUI 145, the user may train the wearable device 105 to recognize when the user has a set time to go to sleep. The wearable go-to-sleep GUI 150 may provide a plurality of selectable or fillable elements through which the user may select and activate when the user wishes to use a previously trained technique, or a sleep aid technique, to go to sleep and activate environmental factors.

A sleep network 171 may include a network software module 175, a network communications module 180, and a network technique info database 185. A sleep network 171 may be administered by a person or entity concerned with the sleep behaviors of others (e.g., a for-profit, non-profit, a research or commercial entity, a wearable device manufacturer, etc.). The network communications 180 module may include executable instructions that, upon execution, are responsible for effectuating communications between the sleep network 171 and the Internet or other intervening network 190. The network software module 175 may control data transmissions to and from the network technique info database 185. The network technique info database 185 may store information about sleep aid techniques, which may be downloaded to the wearable device. While described as a "network" it will be understood that in some embodiments, the functionalities ascribed to the sleep network 171 may be performed by a single device, such as a server or virtual machine operating within a cloud computing environment; as such, the sleep network 171 will be understood to encompass such embodiments as a single device.

While not illustrated, it will be apparent that the various devices 105, 171 in the example system 100 include hardware, such as one or more processors each, to carry out the functionalities described herein. As used herein, the term "processor" will be understood to encompass various hardware devices such as, for example, microprocessors, field-programmable gate arrays (FPGAs), application specific integrated circuits (ASICs), and other hardware devices capable of performing the various functions described herein as being performed by the wearable device 105, sleep network 171, or other device. Further, while not shown, some of the components of these devices 105, 171 (e.g., components 130, 135, 140, 145, 150, 155, 160, 165, 170, 175, 185) will also be understood to be stored among one or more memory devices such as L1/L2/L3 cache, system memory, or storage devices. As used herein, the term "non-transitory machine-readable storage medium" will be understood to refer to both volatile memory (e.g., SRAM and DRAM) and non-volatile memory (e.g., flash, magnetic, and optical memory) devices, but to exclude mere transitory signals. While various embodiments may be described herein with respect to software or instructions "performing" various functions, it will be understood that such functions will actually be performed by hardware devices such as a processor executing the software or instructions in question. In some embodiments, such as embodiments utilizing one or more ASICs, various functions described herein may be hardwired into the hardware operation; in such embodiments, the software or instructions corresponding to such functionality may be omitted.

Figure 1B:
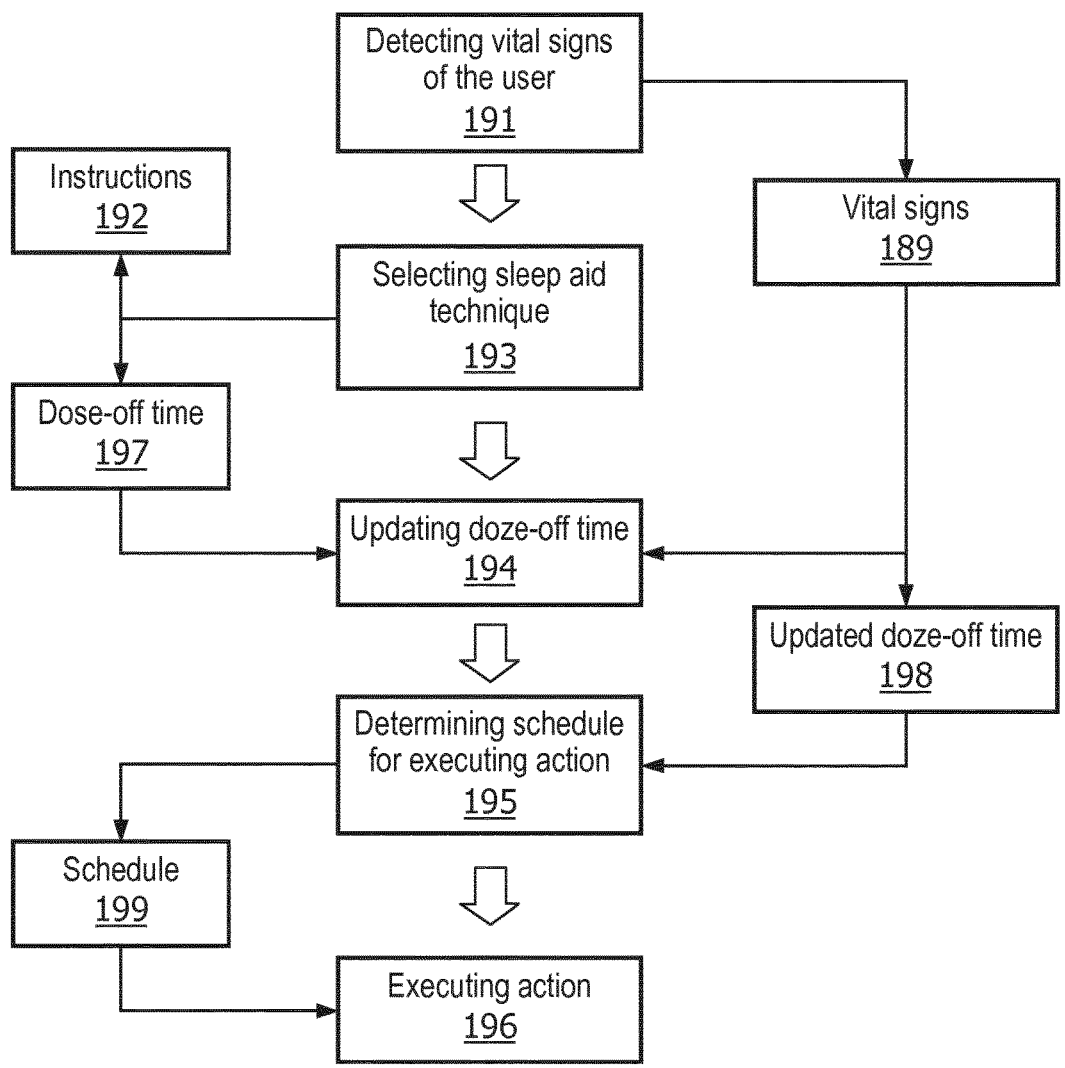
FIG. 1B illustrates a block diagram of a method for sleep assistance to a user of a wearable device according to some embodiments.

FIG. 1B shows a block diagram of a method for sleep assistance to a user of a wearable device according to some embodiments. At least some steps of the method are performed by a processor of the wearable device. The embodiments detect 191 one or several vital signs 189 of the user of the wearable device. For example, the embodiment can detect the vital signs using the sensors 110 and/or 115.

Examples of the vital signs include different types of physiological data of the user such as a pulse and a breathing rate.

The embodiment selects 193 a sleep aid technique associated with one or more instructions 192 facilitating the user to fall asleep and a doze-off time 197, which is a period of time estimated for the sleep aid technique to affect the user following the instructions 192. The selection of the sleep aid technique can be performed by the user using an interface of the wearable device. The interface can include a display device to display a list of the sleep aid techniques available for the user and the instructions of each sleep aid technique. Additionally or alternatively, the interface can include a speaker to pronounce a list of the sleep aid techniques available for the user and the instructions of each sleep aid technique.

The doze-off time can be predetermined and/or learned over time based on tracking the vital signs of the user following the instructions 192. For example, some embodiments add the updated and/or actual doze-off time the user took to fall asleep into a historical sleep data of the selected sleep aid technique. The doze-off time for a subsequent invocation of the sleep aid technique can be determined using the historical sleep data. For example, at least one embodiment determines the doze-off time by averaging multiple updated doze-off times added to the historical sleep data while other embodiments may employ a machine learning technique (e.g., linear regression) to identify a doze-off time based on the sleep aid technique and, potentially, other features such as current or recent physiological parameters (e.g., heart rate, blood pressure, stress level, activity level, etc.) or environmental parameters (e.g., ambient temperature, light, noise, etc.).

In such a manner, a correlation between the vital signs and the doze-off stages of the user is determined for specific actions of the user that wants for fall asleep and is more accurate that a correlation determined for arbitrarily actions. To that end, the embodiment updates 194 the doze-off time based on the vital signs 189 of the user while the user follows the instructions of the sleep aid technique. Next, the embodiment determines 195, based on the updated doze-off time 198, a schedule 199 for executing at least one predetermined action and executes 196 the predetermined action according to the schedule.

For example, the update 194 can be based on differences in physiological conditions of the user on different days, which can be detected based on the vital signs of the user, e.g., according to a correlation between at least some values of the vital signs of the user with fractions of the doze-off time. For example, such a correlation can be a regression function trained during multiple invocations of the sleeping aid technique.

Figure 2A:
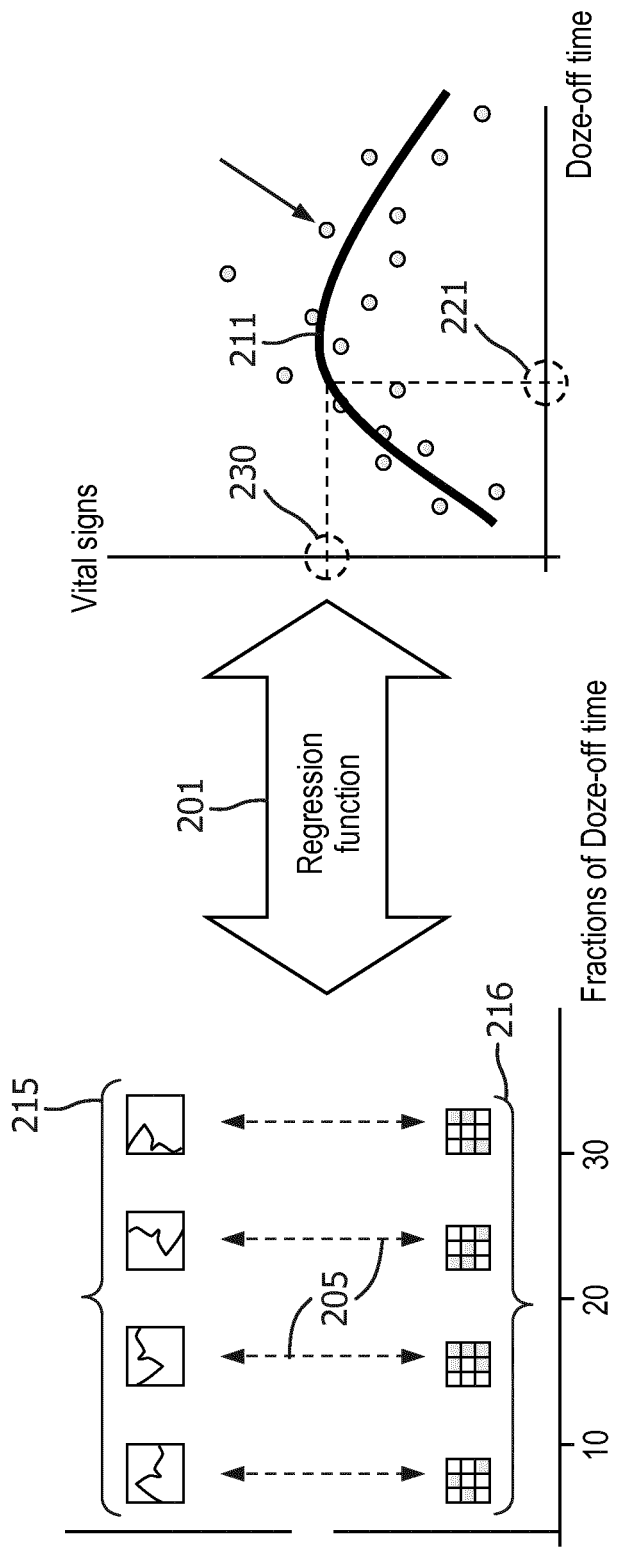
FIG. 2A illustrates a schematic of training a regression function according to some embodiments.

FIG. 2A shows a schematic of training 201 the regression function 211 according to at least one embodiment. The regression function establishes a correspondence 205 between one or more combinations 215 of the values of the vital signs of the user following the instructions of the sleeping aid technique and the fractions of the doze-off time 216 of the sleeping aid technique. Knowing the regression function 211, the particular fraction of the doze-off time can be determined from the particular observations of the values of the vital signs of the user. The regression function 211 can be any complex function. For example, the regression function can be linear, nonlinear, and nonparametric regression function. In some embodiments, the regression function can be a polynomial function or a spline.

At least one embodiment updates the doze-off time based on the regression function 211. For example, if a current value 230 of the vital signs 189 is measured at a half of the doze-off period 197, but corresponds to a third 221 of the doze-off time according to the regression function 211, the doze-off time 197 is updated, such that the two-third of the updated doze-off time 198 remains for the user to follow the instructions, instead of the half of the doze-off time before the update 194.

Additionally or alternatively, at least one embodiment detects the actual time required for the user to fall asleep after selecting the sleep aid technique. This actual time is the updated doze-off time used for scheduling the actions.

Additionally or alternatively, in at least one embodiment the user can select the doze-off time and the method for updating the doze-off time. For example, the user can select the doze-off time as 10 min after the selection the sleep aid technique. The update method can for example increase or decrease the selected doze-off time based on the time of the day when the sleep aid technique is selected and conditions of the user at the time of selecting the sleep aid technique as indicated by the measured vital signs.

Additionally or alternatively, in at least one embodiment, the update can be based on differences in dedication and/or persistence of the user to follow the instruction. For example, the user can select the sleep aid technique, but then decide to stay awake for a little bit longer. To that end, at least one embodiment tracks the actions of the user to extend the doze-off time for a period of time when the user is not following the instructions of the sleep aid technique.

Some embodiments are based on understanding that the memory of the wearable device can store multiple sleep aid techniques associated with different instructions, different doze-off times, and different sensors that can check if the user follows the instructions. For example, the memory of the wearable device can store a set of sleep aid techniques including a first sleep aid technique associated with first vital signs, first instructions and a first doze-off time and a second sleep aid technique associated with second vital signs, second instructions and a second doze-off time. The first vital signs can be different from the second vital signs, the first instructions can be different from the second instructions, and the first doze-off time can be different from the second doze-off time. To that end, when the user selects the sleep aid technique from the set of the sleep aid techniques, some embodiments also selects the specific sensor or combination of the sensors of the wearable devices suitable for tracking the user following the instructions of the selected sleep aid technique.

FIG. 2B illustrates a chart of exemplary relationships among sensors and sleep aid techniques. On the Y-axis, the sensor technique chart 200 may display various sleep aid techniques 210. On the X-axis, the sensor technique chart 200 may display various sensors 220 that may be disposed in the wearable device in various embodiments. The one or more sensors may include both actual sensors (e.g., a microphone 220A or other sensor that actively and directly senses data) and virtual sensors (e.g. a questionnaire 220F displayed to the user by which the wearable device may obtain data despite not directly sensing the data).

The chart illustrates how various sleep techniques may correlate to various sensors (e.g., how various sensors may record a particular sleep technique). The first sleep aid technique displayed in the chart labeled "inhale through left nostril" 210A, for example, may correlate to actual sensors such as a microphone 220A, a camera 220B, an accelerometer 220C, or a virtual sensor such as a questionnaire 220F. Other sleep aid techniques illustrated in the sensor technique chart 200 are "squeeze and relax muscles" 210B, Try to stay awake 210C, Rewind your day 201D, roll your eyes 210E, just imagine 210F, hum to yourself 210G, press here 210H, find your trigger 210J, and make a worry list 210K.

The sensor technique chart 200 illustrates that the foregoing sensors may be used to detect the use and the progress of that particular sleep technique. The microphone 220A may, for instance, detect and record breathing sounds. The camera 220B may record user motion and specifically where a user places his or her hands and the rise and fall of the user's chest and torso. The accelerometer 220C may detect and record the user's motion directly, including the rise and fall of the torso. The questionnaire 220F may request information from the user about how the user is performing the technique and the efficacy of that particular technique. The sensor technique table of FIG. 2 also includes a peripheral device column 220D and a touchscreen column 220E.

The X marks in FIG. 2B illustrate cross reference sleep techniques 210 with sensors and virtual sensors, with peripheral devices 220D, and with a touchscreen 220F. The X marks in the sensor technique table 200 indicate a particular sleep aid technique may use one or more sensors of the sensors 220. These X marks the sensor technique table 200 also identify when a peripheral device 220D or a touchscreen 220E is used with a wearable device. Notice that X marks in the "press here" 210H row of the sensor technique table 200 indicate that the "press here" 210H sleep technique uses a camera 220B, an accelerometer 220C, a peripheral device 220D, a touchscreen 220E, and a questionnaire 220F. The "press here" 210H sleep aid technique may use a touch screen display when touching a series of different points on the touchscreen display when a wearable device monitors the sleepiness of a person using a camera 220B, an accelerometer 220C, a peripheral device 220D, and the touchscreen 220E.

Some embodiments are based on realization that because a correlation between the vital signs and the doze-off stages of the user is determined for the user performing the instructions of the sleeping aid technique, the correlation can include a set of tipping points defining these doze-off stages. For example, the tipping points can correspond to specific fractions of the updated doze-off time and/or to specific values of the vital signs of the user. For example, in at least one embodiment, the tipping points correspond to multiples of quarters of the doze-off period, i.e., one-quarter, two-quarters, three-quarters, and four quarters of the doze-off period. In alternative embodiment, the tipping points correspond to multiples of a specific value of the vital signs. In some embodiments, the tipping points are determined using the regression function 211.

The tipping points allow determining more flexible schedule 199 for execution of the predetermined actions. For example, in at least one embodiment, the schedule prescribes the execution of the action upon the expiration of the doze-off time. In another embodiment, the schedule prescribes the execution of the action after a predetermined amount of time from the expiration of the doze-off time. In yet another embodiment, the schedule prescribes the execution of the action before expiration of the doze-off time, e.g., upon an expiration of a fraction of the doze-off time.

Figures 2C, 3:
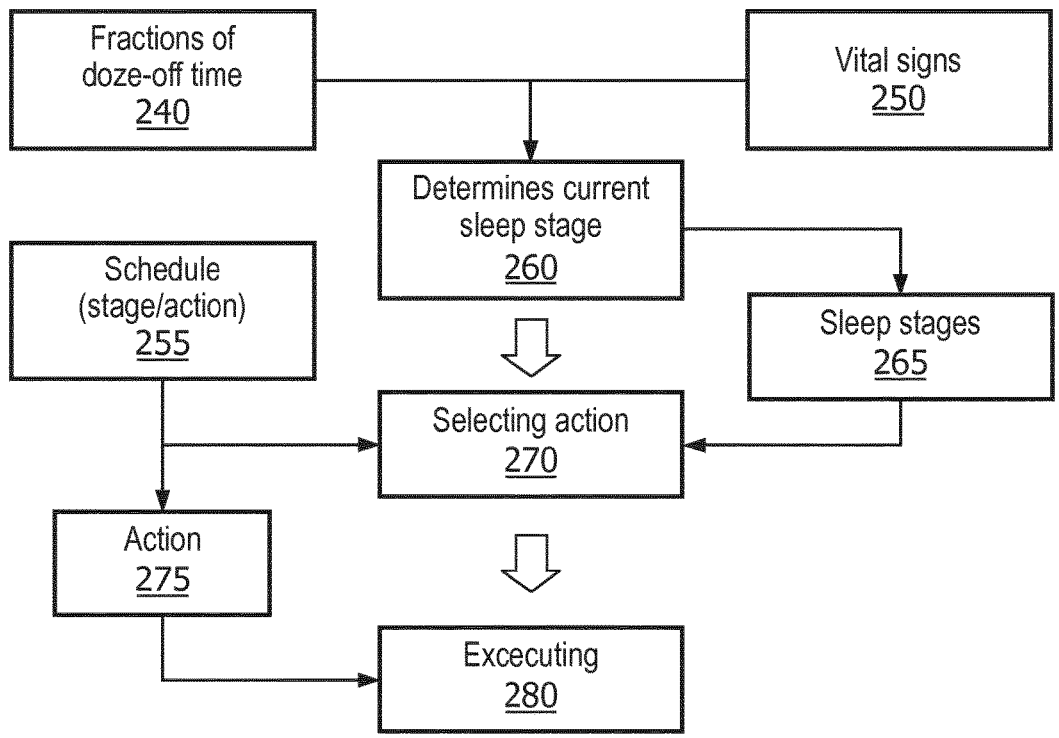
FIG. 2C illustrates a block diagram of a method for selecting an action according to at least one embodiment.
FIG. 3 illustrates an exemplary wearable environment database.

FIG. 2C shows a block diagram of a method for selecting an action according to another embodiment. The embodiment determines a schedule 255 that commands to execute the same or different actions for different tipping points. The schedule 255 can be stored in the memory of the wearable device to define an association between a set of predetermined actions and different doze-off stages.

The embodiment determines 260 a current doze-off stage 265 of the user. For example, the embodiment can select the current doze-off stage based on the values of the vital signs 250 and/or fractions of the doze-of time 240. Next, the embodiment select 270 from the schedule 255 the action 275 corresponding to the current doze-off stage 265 and executes 280 the action 275.

For example, in an embodiment that uses fractions of the doze-of time 240, the different doze-off stages are associated with multiples of a fraction, e.g., a quarter, of the doze-off period. The embodiment tracks the expiration of the time, and selects different doze-off stages upon the expiration of the corresponding multiplication of the fraction of the doze-off time. Additionally or alternatively, the processor can use the current value of the vital signs to select the corresponding fraction of the doze-off time using the regression function 211.

In another embodiment that uses vital signs 250, the doze-off stages are associated with the values of the vital signs and/or specific changes in the values of the vital sings. For example, each sleeps stage is determined when a vital sign of the user doubles its value. Additionally, or alternatively, the sleeping stage can be selected based on one or combination of the values of the vital signs 250 and the expiration of the fraction of the doze-off time 240 using the regression function 211.

FIG. 3 illustrates an exemplary wearable environment database. The wearable environment database may store data concerning actions performable by the wearable device that the user wishes to be taken according to the schedule 199. As shown in the example of FIG. 3, the wearable environmental database may include a data stored in a database table 300 having a plurality of columns. From left to right, the first column may time data 310 representing an amount of time the user wishes to delay the automatic activation of one or more actions after the wearable device determines that the user has begun to fall asleep or "doze off." The second column may include data representing one or more environment triggers 320. The environment triggers 320 may include one or more specific actions performable by the wearable device that the user wants the wearable device to perform after the wearable device determines that the user has begun to fall asleep. For example, in some embodiments, the wearable device may perform actions by communicating with one or more other devices such as controllers for door locks, lights, audio and visual devices, thermostats, etc. Such communication may occur, in some embodiments, via a connected device platform such as the AWS IoT cloud platform.

As shown in row 330 of FIG. 3, for example, the first time after sleep value is zero is linked to the corresponding action of: "lock doors." Based on that data, the wearable device may understand that the user wants the wearable device to transmit a signal that will lock all of the doors of a house without any delay following detection of sleep. The time after sleep value in the second row 340 is 1 and the identified action is "dim all lights to 0," indicating that the user wants the wearable device to automatically dim all the lights in the house to 0 one minute after the wearable device detects sleep. The table also illustrates in row 350 that the user wants the wearable device to "lower all audio device volumes to 0" one minute after the wearable device detects sleep. A user of a wearable device may configure the wearable environmental database to perform other functions.

For example, the predetermined actions can include one or combination of locking or unlocking a door, increasing or decreasing an amount of emitted light, turning an appliance OFF or ON, and increasing or decreasing a volume of an audio emission at an audio device. For example, the predetermined actions can include setting an alarm to ring after eight hours or turning an appliance on (i.e. a coffee maker, an audio device, or auxiliary lighting) after a period of time.

Figure 4:
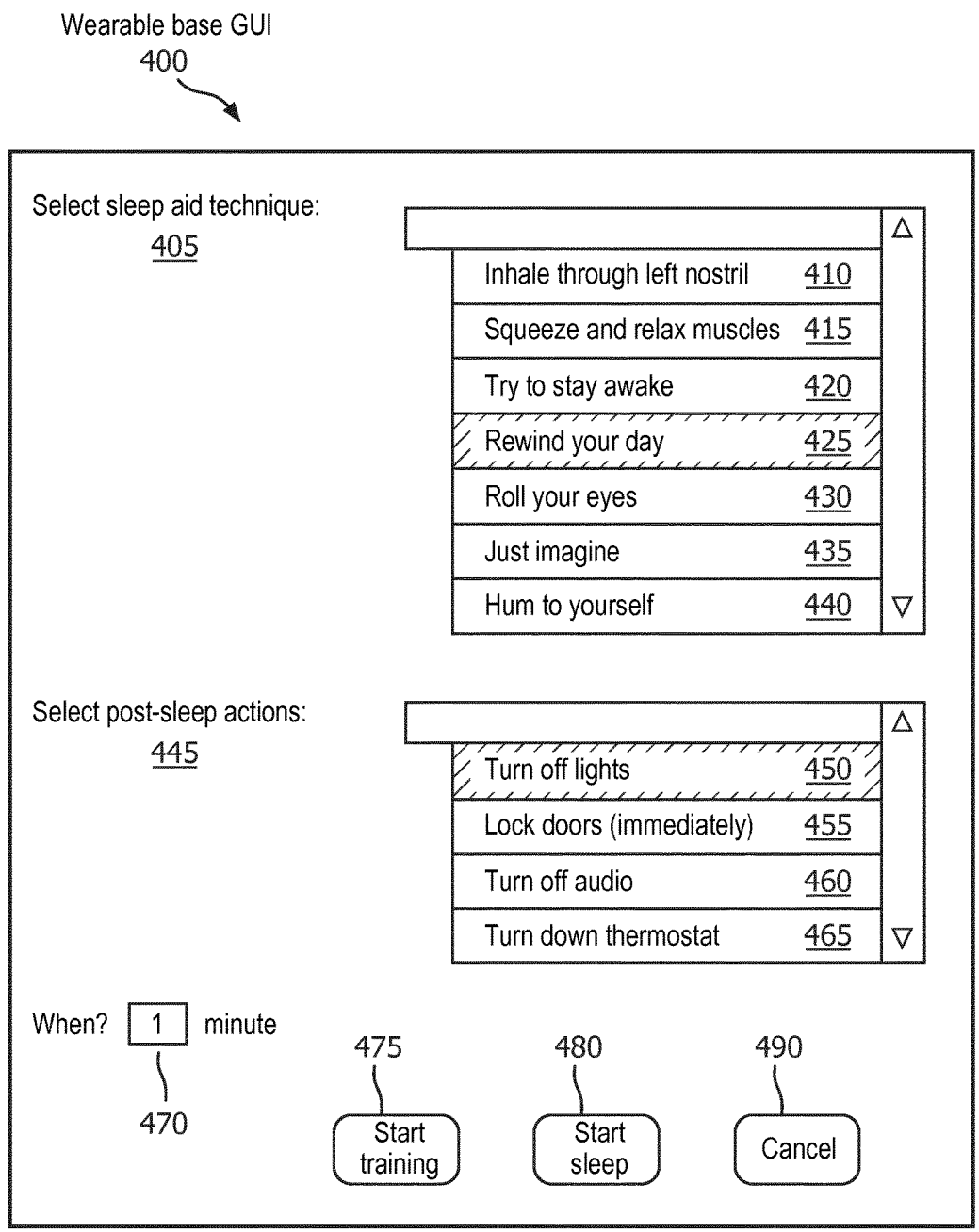
FIG. 4 further illustrates an exemplary wearable device.

FIG. 4 illustrates an exemplary wearable base GUI 400 that may be rendered and displayed on a display of a wearable device or other mobile device (e.g., a smartphone or tablet communicatively coupled to the wearable device). The wearable base GUI 400 may include one or more selectable or fillable elements by which the wearable device may receive data inputted by the user. The selectable or fillable elements may include a select sleep aid technique field 405, a select post-sleep actions field 445, and a time field. The select sleep aid technique field 405 may receive data that may populate the wearable environment database and may be used to activate either the training GUI 400 or the go-to-sleep GUI 400. As shown in the example of FIG. 4, the select sleep aid technique field may include a dropdown menu or the like with one or more selectable techniques items of inhale through left nostril 410, squeeze and relax muscles 415, try to stay awake 420, rewind your day 425, roll your eyes 430, just imagine 435, and hum to yourself 440. The select post-sleep actions field may include a dropdown menu or the like with one or more selectable actions of turn off lights 450, lock doors (immediately) 455, turn off radio 460, and turn down thermostat 465. displayed (e.g., turn off lights). The time field 470 may receive a time value from the user, which may be representative of the amount of time the user wishes the wearable device to delay performing the selected action after the wearable device detects that the user has fallen asleep or "dozed off" (e.g. 1 minute). Upon selection, the action and time selections may be stored in the wearable environment database. In some embodiments, the wearable base GUI 400 may also include one or more selectable elements that, when selected by a user of the wearable device, may cause the wearable device to render and display a different GUI 400 by touching a selection box, such as a wearable training GUI selection box 475, a wearable go-to-sleep GUI 400 selection box 480, or another selection element in GUI 400. The selectable elements may allow a user to navigate between the various available GUIs. The wearable base GUI 400 may be closed when a user selects the cancel selection box 490 of FIG. 4. The wearable base GUI 400 of FIG. 4 provides a user of a wearable device with the ability to select a sleep aid technique and to link an action to the sleep aid technique after the wearable device determines that the user has fallen asleep. For example, the user can select a sleep aid technique 425 and the post-sleep action 450, as shown in FIG. 4.

Figure 5:
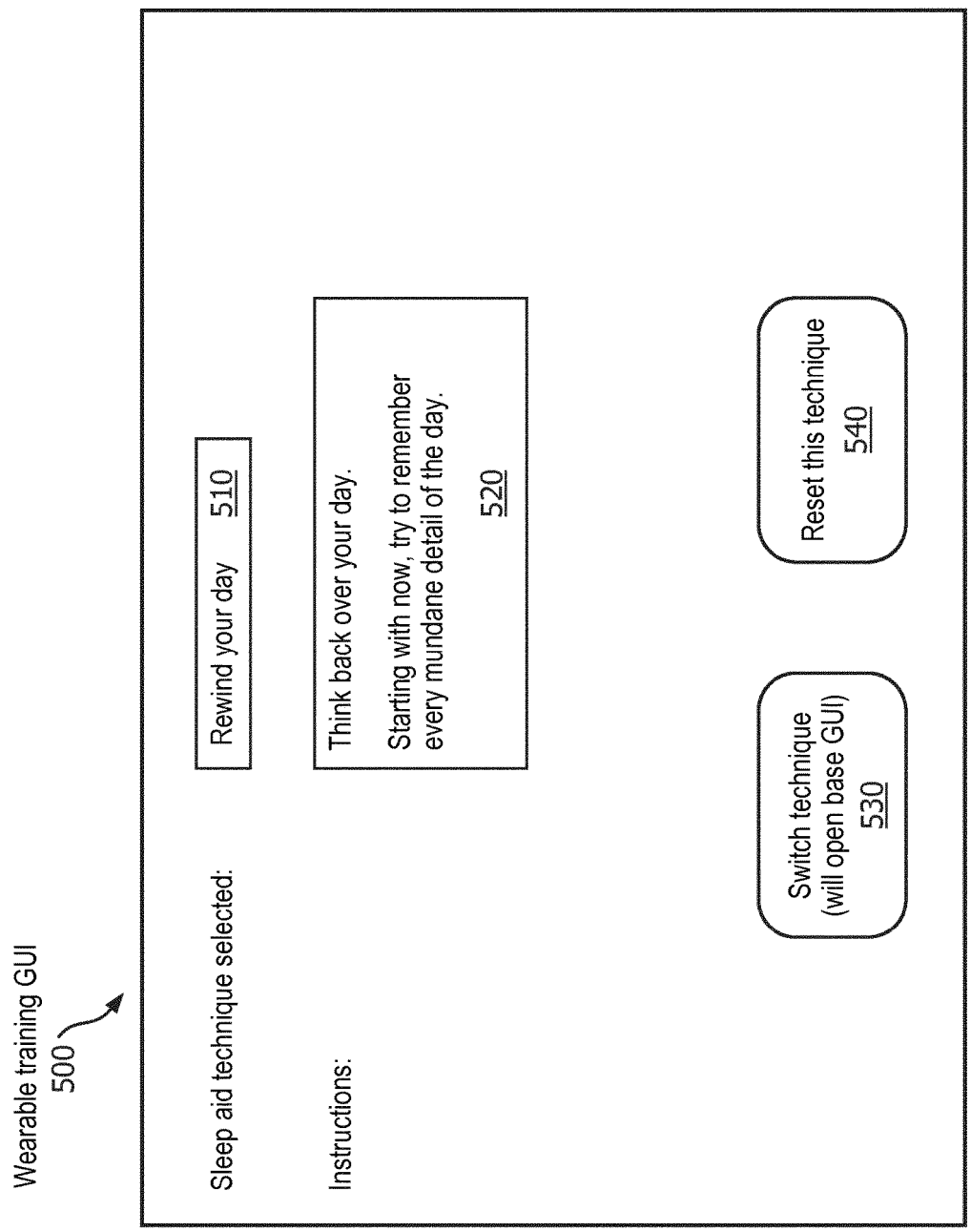
FIG. 5 illustrates an exemplary wearable base graphical user interface ("GUI") that may be rendered and displayed on a display of a wearable device or other mobile device.

FIG. 5 illustrates an exemplary wearable training GUI 500 that may be rendered and displayed on a display of a wearable device or other mobile device (e.g., a smartphone or tablet communicatively coupled to the wearable device). The wearable training GUI 500 may be displayed to the user when the user is training one or more sleep-aid techniques 510. In the example shown in FIG. 5, for instance, the selected sleep-aid technique 510 is "rewind your day." The wearable training GUI may display one or more instructions 520 that the user may follow to perform the selected sleep-aid technique 510 (e.g. "Think back over your day. Starting with now, try to remember mundane detail of the day.").

The wearable training GUI 500 may include one or more additional selectable elements, such as a "switch technique" button 530 and a "reset this technique" button 540. When selected by the user, the switch technique button 530 may switch the sleep-aid technique or navigate the user back to the wearable base GUI and allow the user to select a new technique. When selected by the user, the reset technique button 540 may pull back or rewind the data that has been collected and allow the user to restart the process from the beginning. Pulling back or rewinding the data may include deleting some or all of the data from a database in which the data is stored (e.g., the wearable environment database). The wearable training GUI 500 provides a user of a wearable device with the ability train (or calibrate) a selected sleep aid training technique while collecting data regarding the effectively of the selected sleep aid training technique.

Figure 6:
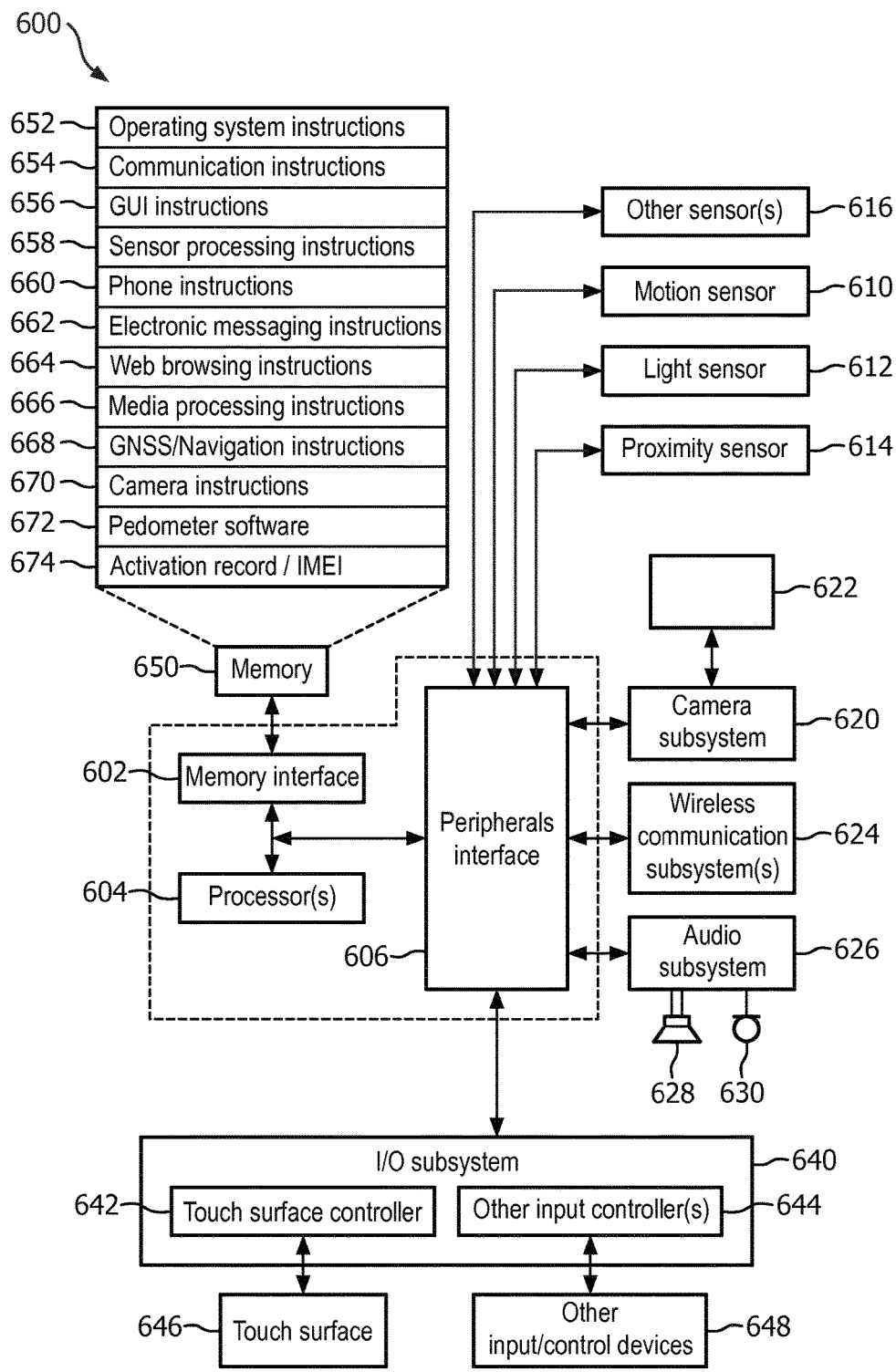
FIG. 6 illustrates an exemplary wearable training GUI that may be rendered and displayed on a display of a wearable device or other mobile device.

FIG. 6 illustrates a mobile device architecture that may be utilized to implement the various features and processes described herein. Architecture 600 can be implemented in any number of portable devices including but not limited to smart wearable devices. Architecture 600 as illustrated in FIG. 6 includes memory interface 602, processors 604, and peripheral interface 606. Memory interface 602, processors 604 and peripherals interface 606 can be separate components or can be integrated as a part of one or more integrated circuits. The various components can be coupled by one or more communication buses or signal lines.

Processors 604 as illustrated in FIG. 6 are meant to be inclusive of data processors, image processors, central processing unit, or any variety of multi-core processing devices. Any variety of sensors, external devices, and external subsystems can be coupled to peripherals interface 606 to facilitate any number of functionalities within the architecture 600 of the exemplar mobile device. For example, motion sensor 610, light sensor 612, and proximity sensor 614 can be coupled to peripherals interface 606 to facilitate orientation, lighting, and proximity functions of the mobile device. For example, light sensor 612 could be utilized to facilitate adjusting the brightness of touch surface 646. Motion sensor 610, which could be exemplified in the context of an accelerometer or gyroscope, could be utilized to detect movement and orientation of the mobile device. Display objects or media could then be presented according to a detected orientation (e.g., portrait or landscape).

Other sensors could be coupled to peripherals interface 606, such as a temperature sensor, a biometric sensor, or other sensing device to facilitate corresponding functionalities. Location processor 615 (e.g., a global positioning transceiver) can be coupled to peripherals interface 606 to allow for generation of geo-location data thereby facilitating geo-positioning. An electronic magnetometer 616 such as an integrated circuit chip could in turn be connected to peripherals interface 606 to provide data related to the direction of true magnetic North whereby the mobile device could enjoy compass or directional functionality. Camera subsystem 620 and an optical sensor 622 such as a charged coupled device (CCD) or a complementary metal-oxide semiconductor (CMOS) optical sensor can facilitate camera functions such as recording photographs and video clips.

Communication functionality can be facilitated through one or more communication subsystems 624, which may include one or more wireless communication subsystems. Wireless communication subsystems 624 can include 802.5 or Bluetooth transceivers as well as optical transceivers such as infrared. Wired communication system can include a port device such as a Universal Serial Bus (USB) port or some other wired port connection that can be used to establish a wired coupling to other computing devices such as network access devices, personal computers, printers, displays, or other processing devices capable of receiving or transmitting data. The specific design and implementation of communication subsystem 624 may depend on the communication network or medium over which the device is intended to operate. For example, a device may include wireless communication subsystem designed to operate over a global system for mobile communications (GSM) network, a GPRS network, an enhanced data GSM environment (EDGE) network, 802.5 communication networks, code division multiple access (CDMA) networks, or Bluetooth networks. Communication subsystem 624 may include hosting protocols such that the device may be configured as a base station for other wireless devices. Communication subsystems can also allow the device to synchronize with a host device using one or more protocols such as TCP/IP, HTTP, or UDP.

Audio subsystem 626 can be coupled to a speaker 628 and one or more microphones 630 to facilitate voice-enabled functions. These functions might include voice recognition, voice replication, or digital recording. Audio subsystem 626 in conjunction may also encompass traditional telephony functions.

I/O subsystem 640 may include touch controller 642 and/or other input controller(s) 644. Touch controller 642 can be coupled to a touch surface 646. Touch surface 646 and touch controller 642 may detect contact and movement or break thereof using any of a number of touch sensitivity technologies, including but not limited to capacitive, resistive, infrared, or surface acoustic wave technologies. Other proximity sensor arrays or elements for determining one or more points of contact with touch surface 646 may likewise be utilized. In one implementation, touch surface 646 can display virtual or soft buttons and a virtual keyboard, which can be used as an input/output device by the user.

Other input controllers 644 can be coupled to other input/control devices 648 such as one or more buttons, rocker switches, thumb-wheels, infrared ports, USB ports, and/or a pointer device such as a stylus. The one or more buttons (not shown) can include an up/down button for volume control of speaker 628 and/or microphone 630. In some implementations, device 600 can include the functionality of an audio and/or video playback or recording device and may include a pin connector for tethering to other devices.

Memory interface 602 can be coupled to memory 650. Memory 650 can include high-speed random access memory or non-volatile memory such as magnetic disk storage devices, optical storage devices, or flash memory. Memory 650 can store operating system 652, such as Darwin, RTXC, LINUX, UNIX, OS X, ANDROID, WINDOWS, or an embedded operating system such as VXWorks. Operating system 652 may include instructions for handling basic system services and for performing hardware dependent tasks. In some implementations, operating system 652 can include a kernel.

Figure 7:
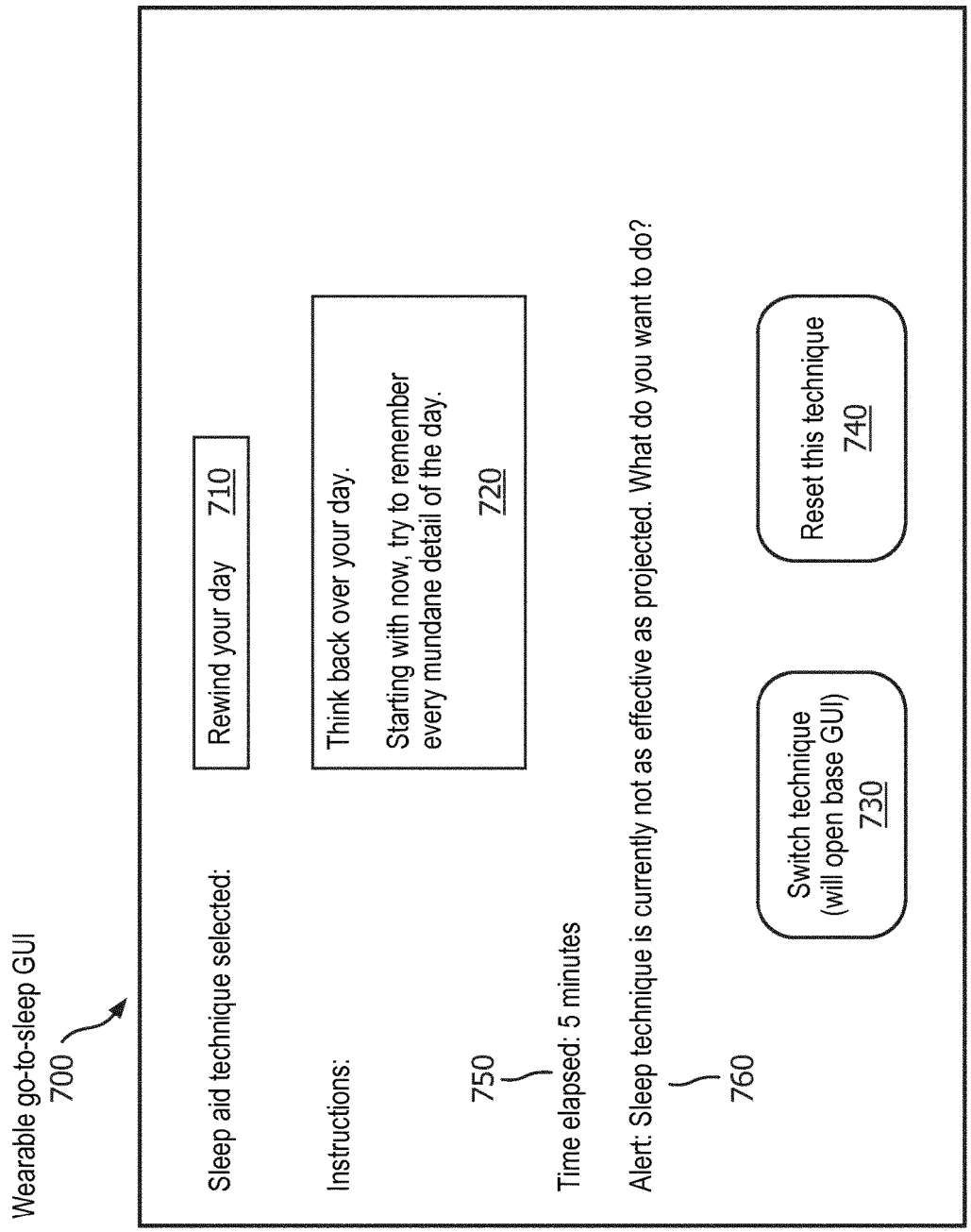
FIG. 7 illustrates an exemplary wearable go-to-sleep GUI that may be rendered and displayed on a display of a wearable device or other mobile device.

Memory 650 may also store communication instructions 654 to facilitate communicating with other mobile computing devices or servers. Communication instructions 654 can also be used to select an operational mode or communication medium for use by the device based on a geographic location, which could be obtained by the GPS/Navigation instructions 668. Memory 650 may include graphical user interface instructions 656 to facilitate graphic user interface processing such as the generation of an interface; sensor processing instructions 658 to facilitate sensor-related processing and functions; phone instructions 660 to facilitate phone-related processes and functions; electronic messaging instructions 662 to facilitate electronic-messaging related processes and functions; web browsing instructions 664 to facilitate web browsing-related processes and functions; media processing instructions 666 to facilitate media processing-related processes and functions; GPS/Navigation instructions 668 to facilitate GPS and navigation-related processes, camera instructions 670 to facilitate camera-related processes and functions; and instructions 672 for any other application that may be operating on or in conjunction with the mobile computing device. Memory 650 may also store other software instructions for facilitating other processes, features and applications, such as applications related to navigation, social networking, location-based services or map displays FIG. 7 illustrates an exemplary wearable go-to-sleep GUI 700 that may be rendered and displayed on a display of a wearable device or other mobile device (e.g., a smartphone or tablet communicatively coupled to the wearable device). The wearable go-to sleep GUI 700 may be displayed to the user when the user is using the wearable device to facilitate the process of falling asleep. In some embodiments, the wearable go-to-sleep GUI 700 may display some or all of the same elements displayed in the wearable training GUI 500. For instance, the wearable go-to-sleep GUI 700 may display the selected sleep-aid technique 710 and one or more instructions 720 that the user may follow to perform the selected sleep-aid technique (e.g. "Think back over your day. Starting with now, try to remember mundane detail of the day."). In some embodiments, additional or alternative media for instruction delivery may be used; for example, audible instructions may be delivered to the user via a speaker of the wearable device or a connected headphone device to avoid the necessity of the user opening their eyes to read textual or other visual instructions. The wearable go-to-sleep GUI 700 may also include one or more additional selectable elements, such as a "switch technique" button 730 and a "reset this technique" button 740. When selected by the user, the switch technique button 730 may switch the sleep-aid technique or navigate the user back to the wearable base GUI and allow the user to select a new technique. When selected by the user, the reset technique button 740 may pull back or rewind the data that has been collected and allow the user to restart the process from the beginning (which may include resetting a clock of the wearable device). Pulling back or rewinding the data may include deleting some or all of the data from a database in which the data is stored (e.g., the wearable environment database). In addition to the elements that may be commonly displayed via the wearable training GUI, the wearable go-to-sleep GUI 700 may display the time elapsed 750 since the selected sleep-aid technique began.

The wearable go-to-sleep GUI may further display an alert 760 when the wearable device has not yet detected sleep after a predetermined amount of time elapses. The predetermined amount of time may be an amount of time before which the user should have fallen asleep if the sleep-aid technique were to be considered effective. When the user does not fall asleep before the predetermined time, the wearable device may alert the user by way of the wearable go-to-sleep GUI 700. The wearable go-to-sleep GUI 700 may display, for example, alert 760 text reading "Sleep technique is currently not as effective as projected. What do you want to do?" The user may then select whether to switch techniques or reset the current technique. The wearable device may receive the user's selection via the one or more selectable elements, such as the switch technique 730 and/or reset technique buttons 740. The wearable training GUI 700 provides a user of a wearable device with the ability to use a selected sleep aid technique while collecting data regarding the effectively of the selected sleep aid technique. The sleep aid technique of FIG. 7 may include the same steps or instructions that were provided by the sleep aid training technique of FIG. 5. In an alternative embodiment, the wearable device, using a processor, can recommend to the user to change the sleep aid technique via the go-to-sleep GUI 700 after the wearable device has recorded that a particular sleep aid technique has been used for a pre-determined number of times already. This is to avoid habituation on a long term. The habituation may hamper the effectiveness of a sleep aid techniques and hence altering between the techniques will further help the user falling asleep.

FIG. 8A illustrates an exemplary wearable software module. The wearable software module may be stored in memory and executed by a processor of the wearable device. To that end, the software modules are codes/instructions executed by one or a combination of the processor of the wearable device and a remote processor, such as the processor of the sleep network 171.

The wearable software module 805 may include a plurality of executable submodules. The software submodules may include a training software submodule 810, an analysis software submodule 815, an environment software submodule 820, and a go-to-sleep software submodule 825. The training software submodule 810 may be responsible for functionality related to training a sleep technique including, e.g., determining the doze-off time 197 and/or the regression function 211. The analysis software submodule 815 may be responsible for functionality related to analysis performed after the training software submodule 810 and/or the go-to-sleep software submodule 825 have been executed. The analysis software submodule 815 may analyze the performance or the efficacy of the sleep-aid technique, e.g., to update the doze-off time 197. The environment software submodule 820 may be responsible for functionality related to activating the environmental changes (e.g., actions performed by the wearable device as dictated by data stored in the wearable environment database). The go-to-sleep software submodule 825 may be responsible for functionality that is performed while the user is attempting to fall asleep.

FIG. 8B illustrates an exemplary process performed upon execution of a wearable software module by a processor of a wearable device. The process may include receiving a signal 835 to initialize the wearable software module 830. The processor may further receive a user selection of a sleep-aid technique 840. The selection may be received by way of the wearable base GUI. The process may include receiving a user selection of a training or go-to-sleep GUIs in step 845. When the user selects the training GUI in step 845, the process may include displaying the training GUI and initiating the training software submodule in step 850. After the training software submodule executes, the process may include initializing the analysis software submodule 855.

When the user selects the go-to-sleep GUI, the process may include displaying the go-to-sleep GUI and initiating the go-to-sleep software submodule 860. The process may then include determining whether the user begins to fall asleep within the predicted time remaining before sleep in step 865. When the user does not begin to fall asleep within the predicted time remaining, the process may include initiating the analysis software submodule in step 870 to re-perform the analysis that generated the time before sleep prediction. When the user begins to fall asleep within the predicted time remaining before sleep, the process may include initiating the environment software submodule in step 875.

Figure 9A:
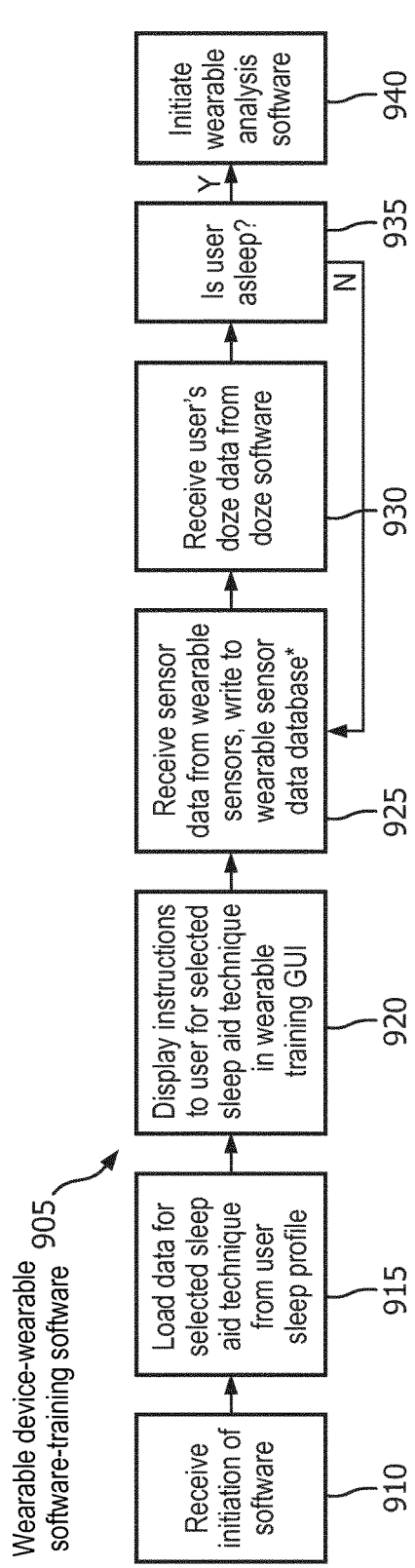
FIG. 9A illustrates an exemplary process performed upon execution of a wearable training software submodule by a processor of the wearable device.

FIG. 9A illustrates an exemplary process performed upon execution of a wearable training software submodule by a processor of the wearable device. In at least one embodiment, the process may include receiving an initiation signal that initializes 910 the training software submodule 905. The process may include loading data representing a selected sleep-aid technique from a memory, e.g., the sleep profile 170 associated with the user of the wearable device in step 915. The process may also include displaying, by way of the wearable training GUI, displaying instructions in step 920 to the user regarding how to perform the selected sleep-aid technique. The process may further include receiving sensor data from the wearable sensors and writing or storing the recorded data to the wearable sensor data database in step 925. The data type that is written may be prefixed by an alphanumeric code indicating which wearable sleep-aid technique has been selected by the user.

The process may include receiving sleep data or "doze data" associated with the user from the doze software module in step 930. The sleep data may be imported directly from the doze software module. For example, the sleep data can include a set of sleep aid techniques and an initial doze-off time for each sleep aid technique. The doze-off times are later updated using, e.g., the training 810 and/or analysis 815 software modules.

The process may further include determining whether the user has fallen asleep in step 935, e.g., upon an expiration of the doze-off time correlated with the vital signs of the user. When the user has fallen asleep, the process may include initiating the wearable analysis software submodule in step 940. When the user has not yet fallen asleep, the process may include returning to the receive sensor data step 925.

Figure 9B:
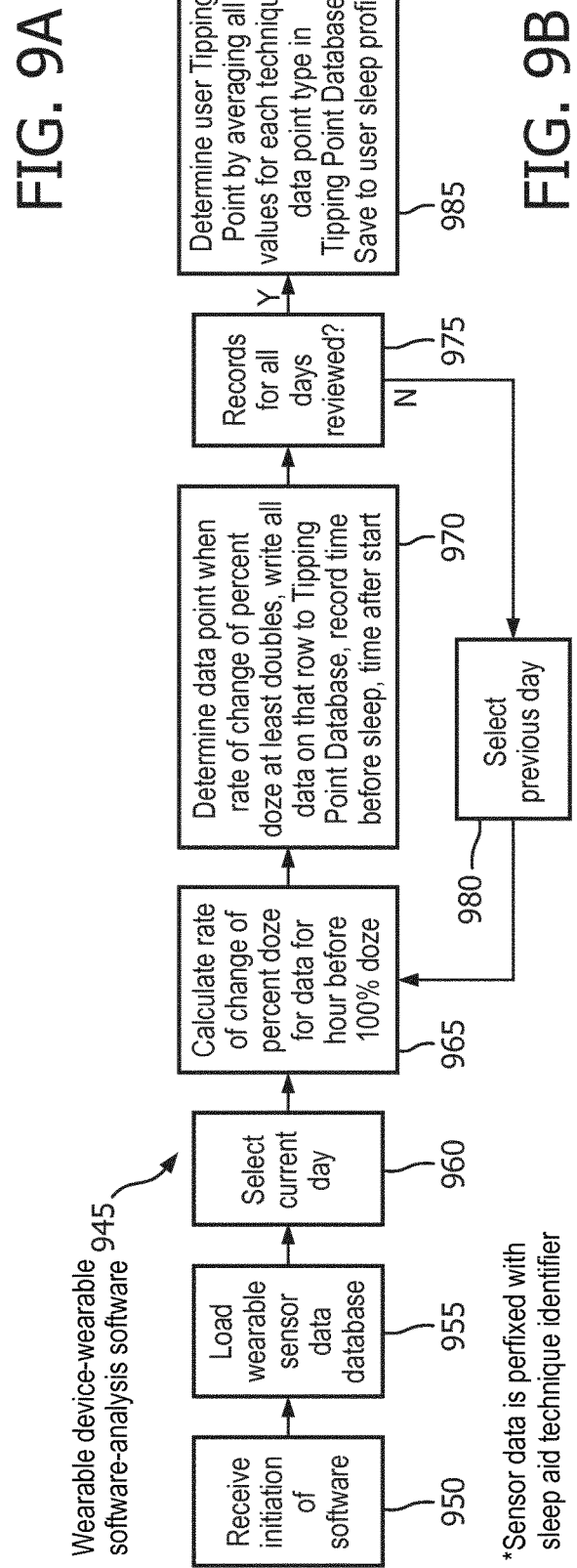
FIG. 9B illustrates an exemplary process performed upon execution of a wearable analysis software submodule by a processor of the wearable device.

FIG. 9B illustrates an exemplary process performed upon execution of a wearable analysis software submodule by a processor of the wearable device. The process performed by the wearable analysis software submodule in step 945 may include receiving an initialization signal that initializes the wearable analysis software submodule in step 950. The process may include loading the wearable sensor data database or otherwise receiving data from the database in step 955. The process may include displaying the current day (or other time information) in step 960. The process may then include calculating a rate of change of a percent dozed value for data for a predetermined time period (e.g., an hour) before reaching a 100 percent doze value in step 965. A 100 percent doze value may signal that the user has fallen asleep. The rate of change indicates the fraction of the doze-off time. For example, 25% rate of change inculcates that the one quarter of the doze-off time has passed. For example, the rate of change can be determined using the regression function 211. Because the falling asleep process is usually not linear, the rate of change can be a useful indication of the effectiveness of the sleep aid technique.

Step 965 of the process may also include tracking the percent doze data received from the doze software module for the preceding predetermined time period (e.g., an hour) from the moment of 100 percent sleep. The process may then include calculating the rate of change of the percent doze data in step 965. The process may then determine 970 the data point representing the time point at which the rate of change of percent doze at least doubles (or exceeds some other predetermine threshold). Step 970 of the process may further include recording the time before sleep and the time of selecting the sleep aid technique.

In some embodiments, the calculated rate of range of percent of doze may be compared to a predetermined threshold. The predetermined threshold may be, for example, the point at which the rate of change at least doubles. The predetermined threshold may be referred to as a "tipping point" after which the user transitions from awake to the beginning of sleep. In such a manner, the tipping points defining the doze-off stages of the user can be determined 970 can be based on the rate of change 965. The data associated with the tipping point may be stored or written to the tipping point database in step 970 of the process along with the time associated with each data point before a 100 percent doze value is reached and also the time associated with each data point from the time the sleep-aid technique is activated. In various embodiments, the predetermined threshold or "tipping point" may vary depending on a variety of factors. Persons of ordinary skill in the art will readily recognize and appreciate that the tipping point described herein is merely illustrative and in no way limiting. Other tipping points may be used.

The process may next include determining whether the records for all days represented in the wearable sensor data database have been reviewed in step 975 of the wearable analysis software 945. When the records for all days represented in the wearable sensor data database have not been reviewed, the processor may include selecting the previous day and repeating prior calculation step (e.g., calculating a rate of change of percent doze for data for an hour prior to 100 percent doze for that day) in step 980. After step 980, the process may move back to step 965, where a rate of change of in the percent doze may be calculated again. When the records for all days represented in the wearable sensor data database have been reviewed in step 975. Then in step 985, the process may include determining the user tipping point by averaging all values for each technique data point type in the tipping point database, and then save the data to a user sleep profile associated with the user. Additional or alternative techniques for determining the user's tipping point may be used in some embodiments. For example, a machine learning approach may be used (e.g., training a linear regression model on the tipping point database) to calculate baseline or user-specific tipping points based on gathered data.

In the tipping point database, as in the wearable sensor data database, each of the sleep-aid technique data point types may be prefixed by an alphanumeric code associated with the sleep-aid technique being used. In such embodiments, when the processor includes averaging all the values for each technique data point type, the processor involves averaging those data point types with those prefixes only for the specified type of data for the specified sleep-aid technique. When all the tipping points have been averaged, that data may be the average point at which the user is predicted to fall asleep. The data may be sent to the user sleep profile and recorded in a row associated with that user sleep-aid technique.

Figure 10A:
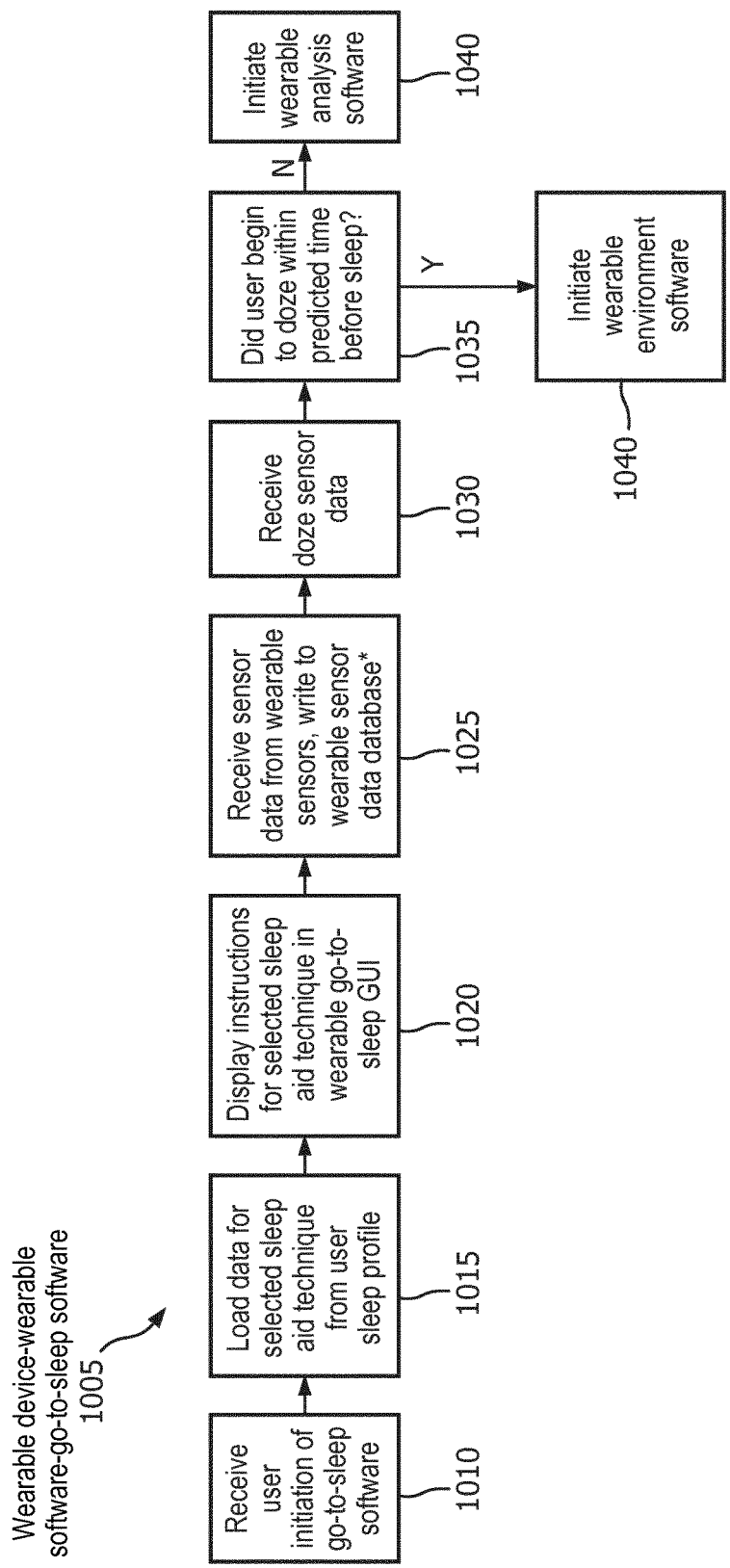
FIG. 10A illustrates an exemplary process performed upon execution of a wearable go-to-sleep software submodule by a processor of the wearable device.

FIG. 10A illustrates an exemplary process performed upon execution of a wearable go-to-sleep software submodule by a processor of the wearable device. In at least one embodiment, the process of the wearable go-to sleep software 1050 may include step 1010, where an initiation signal that initializes the go-to-sleep software submodule is received. The process may include loading data for a selected sleep-aid technique from a user sleep profile in step 1015. The data may originate from a sleep profile 170 that has been previously analyzed and written during execution of the analysis software submodule. The process may include displaying, by way of the go-to-sleep GUI, instructions to user regarding how to implement a selected sleep-aid technique in step 1020. The process may further include step 1025, where sensor data is received from the wearable sensors and writing or storing the recorded data to the wearable sensor data database. The data type that is written may be prefixed by an alphanumeric code indicating which wearable sleep-aid technique has been selected by the user. The process may include step 1030, where sleep data or "doze data" associated with the user from the doze software module is received by the wearable go-to sleep software 1005. The sleep data may be imported directly from the doze software module. The process may further include determining whether the user began to fall asleep or "doze" within the predicted time before sleep in step 1035. The process may effectively include determining whether the prediction made by the analysis software submodule was accurate. When the user began to fall asleep within the predicted time before sleep, the wearable environment software submodule may be executed in step 1040 of the wearable go-to sleep software 1005. When the user did not begin to fall asleep within the predicted time before sleep, the analysis software submodule may be executed in step 1045.

Figure 10B:
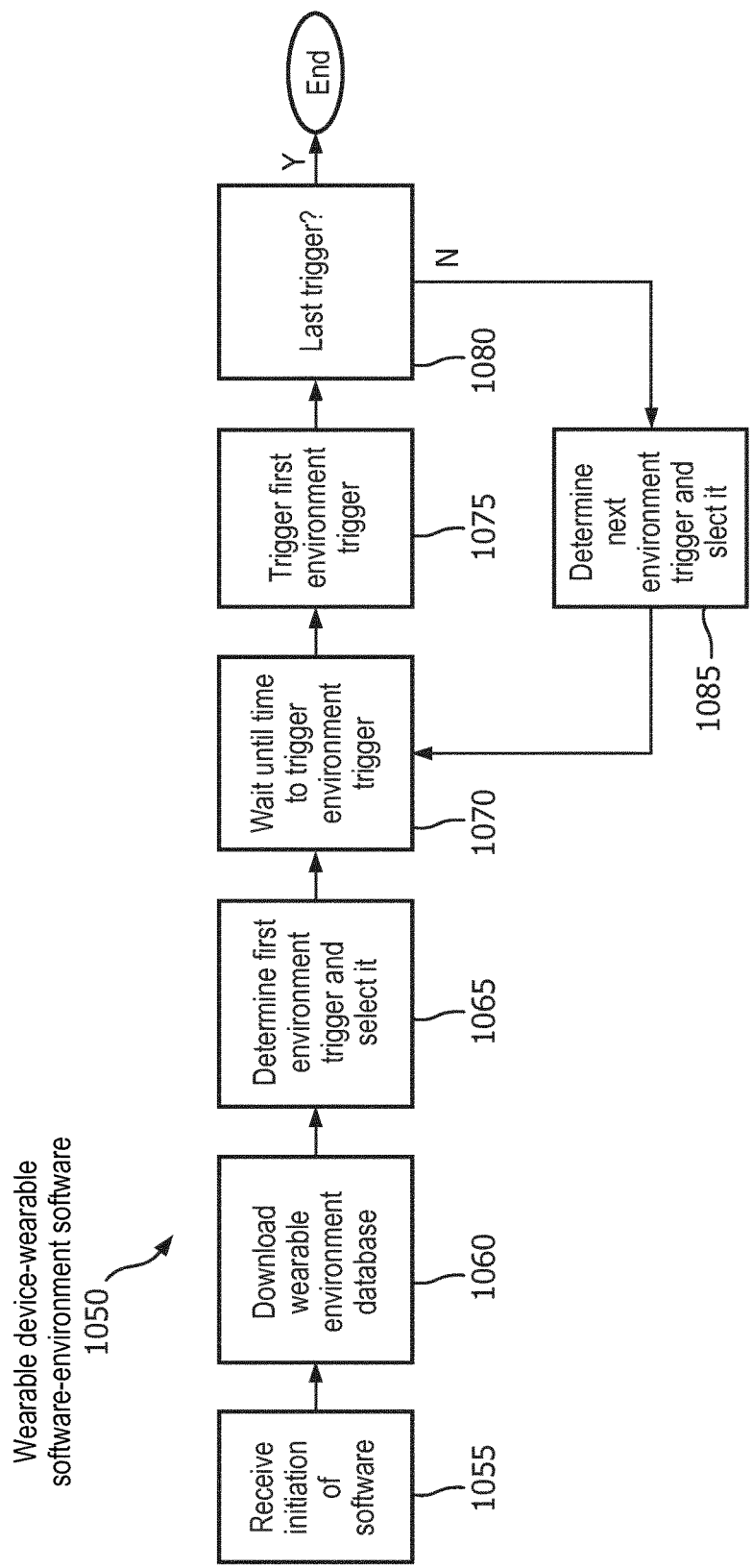
FIG. 10B illustrates an exemplary process performed upon execution of a wearable environment software submodule by a processor of the wearable device.

FIG. 10B illustrates an exemplary process performed upon execution of a wearable environment software submodule by a processor of the wearable device. In at least one embodiment, the process of the wearable environment software submodule in step 1050 may include receiving an initiation signal that initializes the environment software submodule in step 1055. The process may further include downloading or otherwise accessing data stored in the wearable environment database in step 1060. The process may include determining and selecting a first environment trigger (e.g. the trigger that correlates to the first or the lowest number in the time after sleep column of the stored table) in step 1065. The process may include waiting until the specified time after sleep has elapsed in step 1070 to trigger the environment trigger (i.e., perform the specified action) in step 1075. The process then determines whether the performed trigger was the last trigger stored in the wearable environment database in step 1080. When the performed trigger was the last trigger, the environment software submodule may stop executing. When the performed trigger was not the last trigger stored in the environment database, the process may loop back to step 1070 to further await a time trigger or an environmental trigger.

FIG. 11 illustrates an exemplary wearable sensor data database. The wearable sensor data database 1100 may store data recorded by the one or more wearable sensors disposed in the wearable device (e.g., the doze sensor). The wearable sensor data database may further store data provided by one or more software modules (e.g., the doze software module). The database shown in the exemplary embodiment of FIG. 11 contains data arranged in a plurality of columns—date 1110, time 1120, percent dozed 1130, technique data type 1 1140, technique data point 1 1150, technique data type n 1160, and technique data point n 1170. The date and time columns may store the date and the time at which sensor data was recorded. The data and time data may be received from a system clock disposed in the wearable device. The table of wearable sensor data base data 1100 may also include a plurality of rows 1180 where each row in the table 1100 may be associated with a date 1110, a time 1120, a percent dozed 1130, a technique data type 1 1140, a technique data point 1 1150, a technique data type n 1160, and a technique data point n 1170.

The percent dozed 1130 column may store data received from the doze sensor and/or the doze software module. The percent dozed data may indicate how asleep the user is with respect to a completely asleep value of 100 percent dozed (i.e. asleep). The Technique Data Type 1 column 1140 may store information identifying the type of data being recorded. The data type may include a unique prefix associated with each sleep-aid technique (e.g., a unique prefix of "RWYD" is associated with the sleep-aid technique named "rewind your day.") The label "pulse" indicates that pulse data is being recorded. The Technique Data Point 1 1150 column may store actual data points. For instance, as shown in FIG. 11, the value 64 indicates that the pulse value is 64 beats per minute. The data may be stored at a predetermined interval (e.g., once per minute, or a longer or shorter interval).

The last two columns labeled Technique Data Type N 1160 and Technique Data Point N 1170 may represent any subsequent data types that may be recorded in relationship to the sleep-aid technique. In the example shown, the data type is blood pressure as indicated by the unique identified "BP." The sleep-aid technique is "rewind your day" as indicated by the identifier "RWYD." There may be one or any number of additional data types that may be recorded for each sleep-aid technique. The examples provided are merely illustrative and in no way limiting. The wearable sensor database table 1100 may be used to store data associated with dates and times, the stored data may include a pulse rate, a measure of blood pressure, a percent doze, and may identify a sleep aid technique used by a user of the wearable device.

FIG. 12 illustrates an exemplary wearable tipping point database. The wearable tipping point database 1200 may store data provided by the analysis software submodule. The data may relate to the moment during training or go-to-sleep software submodule usage at which the rate of doze began to rapidly increase. The database may store data in an arrangement similar to that described in FIG. 11 (including a date column 1210 and a time column 1220). In some embodiments, additional data columns may be present, such as "time before sleep" 1230 and "time after start" 1235. The date 1210 and time columns 1220 may store data indicating the date and time at which sensor data was stored. As shown in FIG. 12, the data in the date 1210 and time 1220 columns indicate that the user falls asleep around the same time each night (approximately 9:00 PM). The time before sleep column 1230 may store an amount of time that passes between when the user has selected the sleep aid technique and when the 100 percent doze value was reached for that sleep session. The time after start column 1235 may store the amount of time that passes between the selection of the sleep aid technique and the time when the user starts to follow the instructions. The remaining columns percent doze 1240, technique data type 1 1245, technique data point 1 1250, technique data type n 1255, and technique data point n 1260 may store data as described with respect to FIG. 11. The stored data points (i.e., technique data points 1 through n) may be averaged for each technique data type to update the doze-off time. Time before sleep and time after start may also be averaged to create an average time before sleep that the user should reach those particular average data points. All of the foregoing data may be stored in a user sleep profile associated with the user. The wearable tipping point database table 1200 may also be used to store data associated with dates and times, the stored data may include a pulse rate, a measure of blood pressure, a percent doze, and may identify how effective a particular sleep aid technique used by a user of the wearable device is.

FIG. 13 illustrates an exemplary wearable user sleep profile. The wearable user sleep profile may include information related to each sleep-aid technique. In the embodiment shown in FIG. 13, the user sleep profile information is arranged in a plurality of columns in a table 1300. The first column may store information identifying the sleep-aid techniques 1310 that have been downloaded by the user to the wearable device. The next column 1320 may store data indicating the doze-off time for each particular sleep-aid technique. As previously discussed, the predicted time before sleep may be calculated (e.g., as an average value) using data stored in the tipping point database. FIG. 13 illustrates that different doze off times are associated with different sleep-aid techniques. Some of the techniques may not include data where the user has not yet trained those particular techniques (i.e., there is not data upon which the wearable device may perform a prediction yet). The next column 1330 may indicate a predicted time after start at which the user is predicted to achieve the tipping point. Each sleep aid technique can be associated with multiple tipping points. FIG. 13 illustrates that different times after start are associated with different sleep-aid techniques. Some of the techniques may not include data where the user has not yet trained those particular techniques (i.e., there is not data upon which the wearable device may perform a prediction yet). The next columns may include Technique Data Type 1 1340 and Technique Average Data Point 1 data 1350, which may identify data types and the average data points from the tipping point databases after the averaging calculation. The user sleep profile table may also include column 1370 that stores data relating to technique average data point n, and column 1380 that stores instructions that may be displayed on a display at the wearable device. Notice that instructions in column 1380 of the wearable user sleep profile table 1300 include various types of actions or exercises that may help a person prepare to quickly fall asleep. For example, the second to last entry in column 1380 relates to the sleep aid technique of "take a breather" where the user instructions displayed in a GUI instruct the user of the wearable device to "Synch your breath synchronizer device. Breathe in and out with the device." The wearable device may thus provide instructions that are synchronized with actions displayed on the display at the wearable device. While these actions may be displayed on a display, they may alternatively be provided over a speaker. In the instance where a speaker is used, the speaker may emit the word "inhale" and "exhale" when synchronizing the user's breaths with breath timing provided by the wearable device.

As shown in FIG. 13, the unique prefixes may be associated with different data types. Different data types may be associated with different sleep-aid techniques are listed in a series of rows 1390. The rows included in the wearable user sleep profile table 1300 include the same sleep aid techniques that were described in respect to FIG. 2. For example, "inhale through left nostril" may be associated with respiration and blood pressure as its two data types. "Rewind your day," on the other hand, is associated with pulse and blood pressure data types, while "roll your eyes" is associated with only eye roll data and has no other data type. The various data points stored in this database may be derived as averages of the various entries in the tipping point database for that data type in column 1370. In other embodiments, other calculations may be used.

The final column 1380 in the database may store instructions to be provided to a user of the wearable device. The instructions may be displayed to the user by way of the training GUI, the go-to-sleep GUI, or another GUI. The instructions may advise a user regarding how to implement a selected sleep-aid technique. As shown in the provided embodiment, the instructions are text-based instructions designed to be read by a user. In other embodiments, the instructions may be presented in other formats (e.g., audio, video) and may be interactive. The instructions may include HTML, JavaScript, or other programming provides interactive functionalities.

Figure 14:
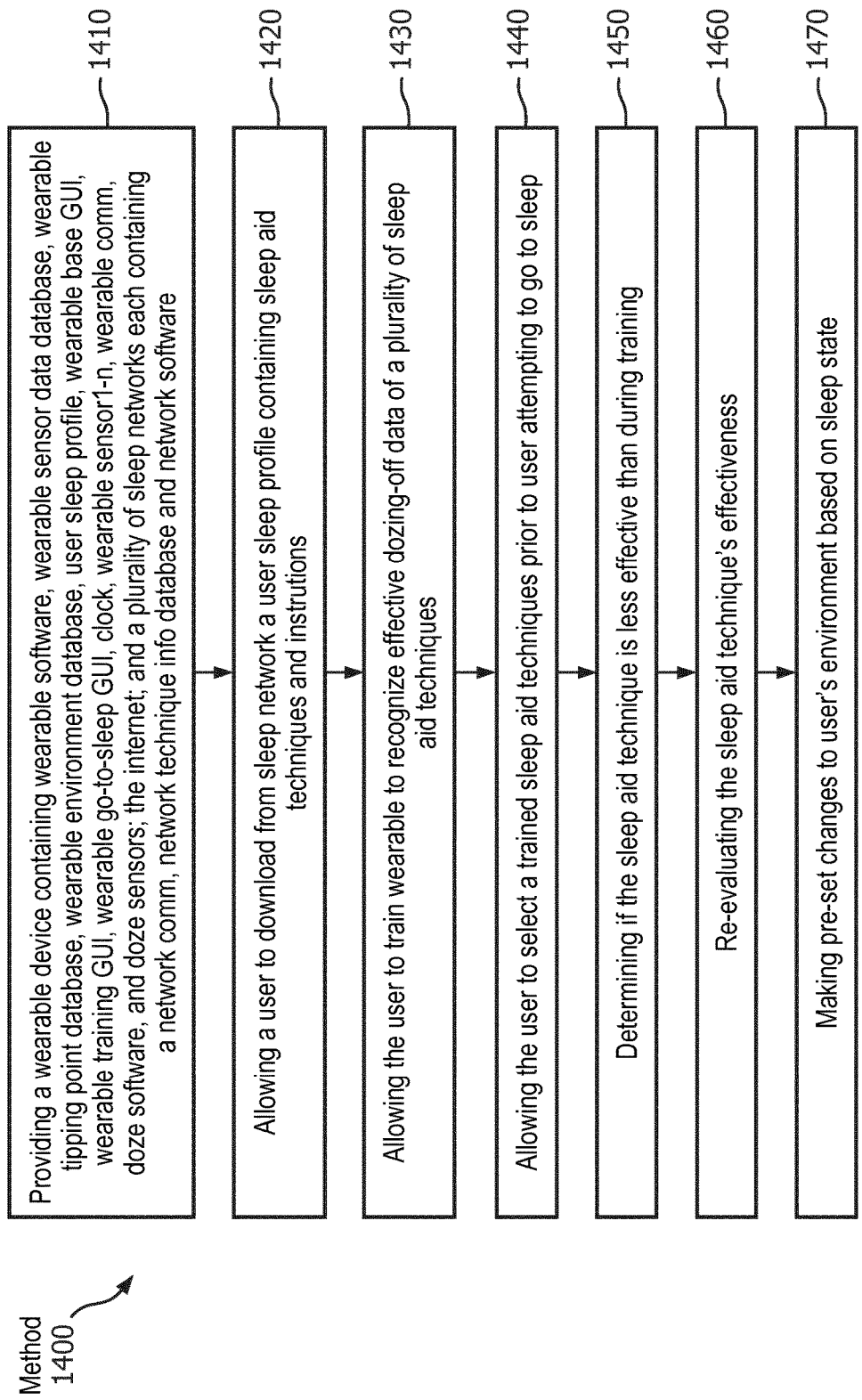
FIG. 14 illustrates an exemplary method for predicting when a wearable device user will fall asleep based on previously recorded and received sleep data.

FIG. 14 illustrates an exemplary method for predicting when a wearable device user will fall asleep based on previously recorded and received sleep data. The method 1400 may include providing a wearable device, a network, and a sleep network like those described in the context of FIG. 1 in step 1410. The method may include downloading a user sleep profile from the sleep network. The user sleep profile may include sleep-aid techniques and corresponding instructions in step 1420. The method may further include training the wearable device to recognize effective sleep data produced while applying a plurality of different sleep-aid techniques in step 1430. The method may include receiving a user selection of a sleep-aid technique to be trained prior to the user attempting to fall asleep in step 1440. The method may include determining whether the sleep-aid technique is less effective (i.e., associated with a low sleep-aid technique efficacy metric) than during training in step 1450. The method may further include re-evaluating a sleep-aid technique's effectiveness in step 1460. The method may include performing predetermined actions that relate to the user's environment based on the user's sleep state and various timing considerations in step 1470.

The foregoing detailed description has been presented for purposes of illustration and description. It is not intended to be exhaustive or to limit the technology to the precise form disclosed. Many modifications and variations are possible in light of the above teaching. The described embodiments were chosen in order to best explain the principles of the technology and its practical application to enable others skilled in the art to best utilize it in various embodiments and with various modifications as suited to the particular design considerations at issue (e.g., cost, availability, preference, etc.). The scope of the technology should be defined only by the claims appended to this description.

The invention claimed is:

1. A wearable device for sleep assistance, comprising:
   at least one sensor to detect one or several vital signs of a user of the wearable device;
   a memory to store a set of sleep aid techniques,
   each sleep aid technique includes instructions facilitating the user to fall asleep and is associated with a doze-off time estimated for the sleep aid technique to affect the user following the instructions;
   an interface to receive a selection of a sleep aid technique from the set of sleep aid techniques and to render the instructions of the selected sleep aid technique to the user; and
   a processor to update the doze-off time based on the vital signs of the user, to determine, based on the updated doze-off time, a schedule for executing at least one predetermined action, and to execute the predetermined action according to the schedule.

2. The wearable device of claim 1, wherein the processor adds the updated doze-off time into a historical sleep data of the selected sleep aid technique and determines the doze-off time for a subsequent invocation of the selected sleep aid technique using the historical sleep data.

3. The wearable device of claim 2, wherein the processor determines the doze-off time by averaging multiple updated doze-off times added to the historical sleep data.

4. The wearable device of claim 1, wherein the processor selects the sensor from a set of sensors of the wearable device configured to track actions of the user following the instructions and extends the doze-off time when the user, after the selection of the sleep aid technique, is not following the instructions.

5. The wearable device of claim 1, wherein the processor updates the doze-off time based on a correlation between at least some values of the vital signs of the user with fractions of the doze-off time.

6. The wearable device of claim 1, wherein the memory stores a set of sleep aid techniques including a first sleep aid technique associated with first vital signs, first instructions and a first doze-off time and a second sleep aid technique associated with second vital signs, second instructions and a second doze-off time, wherein the first vital signs are different from the second vital signs, the first instructions are different from the second instructions, and wherein the first doze-off time is different from the second doze-off time.

7. The wearable device of claim 1, wherein the interface includes one or combination of a display device to display the instructions of the sleep aid technique and a speaker to pronounce the instructions of the sleep aid technique.

8. The wearable device of claim 1, wherein at least one predetermined action include one or combination of locking or unlocking a door, increasing or decreasing an amount of emitted light, turning an appliance OFF or ON, and increasing or decreasing a volume of an audio emission at an audio device.

9. The wearable device of claim 1, wherein the memory stores a set of tipping points defining doze-off stages of the user and stores a set of predetermined actions associated with different doze-off stages, wherein the processor determines a current doze-off stage of the user based on current values of the vital signs and executes the predetermined action associated with the current doze-off stage.

10. A method for sleep assistance to a user of a wearable device, comprising:
    detecting one or several vital signs of the user of the wearable device;
    selecting a sleep aid technique associated with one or more instructions facilitating the user to fall asleep and a doze-off time estimated for the sleep aid technique to affect the user following the instructions;
    updating the doze-off time based on the vital signs of the user;
    determining, based on the updated doze-off time, a schedule for executing at least one predetermined action; and
    executing the predetermined action according to the schedule, wherein at least some steps of the method are performed by a processor of the wearable device.

11. The method of claim 10, further comprising:
    adding the updated doze-off time into a historical sleep data of the sleep aid technique; and
    determining the doze-off time for a subsequent selection of the sleep aid technique using the historical sleep data.

12. The method of claim 10, wherein the selecting comprises:
    acquiring a set of sleep aid techniques including a first sleep aid technique associated with first instructions and a first doze-off time and a second sleep aid technique associated with second instructions and a second doze-off time, wherein the first instructions are different from the second instructions, and wherein the first doze-off time is different from the second doze-off time;

rendering the set of sleep aid techniques on a graphic user interface (GUI) of the wearable device;

receiving a selection of the first sleep aid technique in response to the rendering.

13. The method of claim 10, further comprising:

tracking actions of the user following the instructions of the sleep aid technique;

and extending the doze-off time when the user, after the selection of the sleep aid technique, is not following the instructions.

14. The method of claim 10, wherein at least one predetermined action include one or combination of locking or unlocking a door, increasing or decreasing an amount of emitted light, turning an appliance off or on, and increasing or decreasing a volume of an audio emission at an audio device.

15. A non-transitory computer readable storage medium including a program embodied thereon executable by a processor for performing a method, the method comprising:

detecting one or several vital signs of a user of a wearable device;

selecting a sleep aid technique associated with one or more instructions facilitating the user to fall asleep and a doze-off time estimated for the sleep aid technique to affect the user following the instructions;

updating the doze-off time based on the vital signs of the user;

determining, based on the updated doze-off time, a schedule for executing at least one predetermined action; and executing the predetermined action according to the schedule.

* * * * *